(12) United States Patent
Márton et al.

(10) Patent No.: US 7,863,046 B2
(45) Date of Patent: Jan. 4, 2011

(54) METHOD FOR MICROPROPAGATION OF MONOCOTS BASED ON SUSTAINED TOTIPOTENT CELL CULTURES

(75) Inventors: László Márton, Chapin, SC (US); Mihaly Czako, Columbia, SC (US)

(73) Assignee: The University of South Carolina, Columbia, SC (US)

(*) Notice: Subject to any disclaimer, the term of this patent is extended or adjusted under 35 U.S.C. 154(b) by 206 days.

(21) Appl. No.: 11/800,719

(22) Filed: May 7, 2007

(65) Prior Publication Data

US 2008/0282424 A1 Nov. 13, 2008

(51) Int. Cl.
C12N 5/00 (2006.01)
C12N 5/02 (2006.01)

(52) U.S. Cl. .................. 435/410; 435/420; 435/430

(58) Field of Classification Search ............ 435/410, 435/420, 430
See application file for complete search history.

(56) References Cited

U.S. PATENT DOCUMENTS

| 6,389,746 | B1 | 5/2002 | Bransby |
| 6,821,782 | B2* | 11/2004 | Marton et al. ............... 435/430 |
| 7,052,912 | B1 | 5/2006 | Woods et al. |

FOREIGN PATENT DOCUMENTS

| EP | 0861589 A1 | 9/1998 |
| WO | WO 95/26628 | 10/1995 |
| WO | WO 01/56368 A1 | 8/2001 |
| WO | WO 02/14520 A2 | 2/2002 |
| WO | WO 02/063023 A2 | 8/2002 |
| WO | WO 02/063023 A3 | 8/2002 |
| WO | WO 02/063024 A2 | 8/2002 |
| WO | WO 02/063024 A3 | 8/2002 |
| WO | WO 03/020014 A2 | 3/2003 |

OTHER PUBLICATIONS

Shariatpanahi et al. "Stresses applied for the re-programming of plant microspores towards in vitro embryogenesis," Physiologia Plantarum 127: pp. 519-534, 2006-(published Apr. 26, 2006).*

(Continued)

*Primary Examiner*—Susan B McCormick Ewoldt
(74) *Attorney, Agent, or Firm*—Myers Bigel Sibley & Sajovec P.A.

(57) ABSTRACT

The present invention provides a method of micropropagating a monocotyledonous plant comprising: (a) cultivating an explant of tissue from a monocotyledonous plant shoot tip on a primary medium, wherein the explant has been pretreated with a cold temperature and the primary medium comprises auxin or auxin and cytokinin, to produce a totipotent embryogenic cell culture; (b) treating the totipotent embryonic cell culture with a cold temperature; (c) maintaining the totipotent embryogenic cell culture by cultivation on a secondary medium, whereby a totipotent embryogenic cell culture of a monocotyledonous plant is produced and maintained; and (d) transferring the embryogenic cell culture of step (c) to a tertiary medium to continue multiplication and to produce a plantlet with roots and shoots, thereby micropropagating a monocotyledonous plant. The micropropagation techniques described herein provide plants for such purposes as development of elite plant lines, phytoremediation and biomass production.

27 Claims, 9 Drawing Sheets

OTHER PUBLICATIONS

Tsugawa et al. "A low-temperature method for maintaining plant regeneration activity in embryogenic callus of rice (*Oryza sativa* L.)" Plant Cell Reports (2000) 19:371-375.*

Hansen et al. "Short-term in vitro storage of *Miscanthus* x *ogiformis* Honda 'Giganteus' as affected by medium composition, temperature and photon flux density," Plant Cell, Tissue and Organ Culture 49: pp. 161-169, 1997.*

Shibli et al. "In Vitro Conservation and Cryopreservation of Plant Genetic Resources: A Review," World Journal of Agricultural Sciences 2 (4): 372-382, 2006.*

Lewandowski, "Micropropagation of *Miscanthus* x *giganteus*," in Biotechnology in Agriculture and Forestry 39 pp. 239-255, Y.P.S. Bajaj, ed., Springer-Verlag Berlin Heidelberg, NY (1997).

Lewandowski et al., "Development of a Tissue Culture System with Unemerged Inflorescences of *Miscanthus* 'Giganteus' for the Induction and Regeneration of Somatic Embryoids," *Beitr. Biol. Pflanzen* 67: 439-451 (1993).

Examination of Various Cultivation Techniques for *Miscanthus giganteus* for Improving the Young Plants' Ability to Survive the Winter as well as for Reducing the Costs for Setting up Crop Stands, *Proceedings of the 10th European Conference for Biomass for Energy and Industry*, Würzburg, Germany, Jun. 1998, pp. 947-950 (1998).

Holme et al., "Callus Induction and Plant Regeneration from Different Explant Types of *Miscanthus* x Ogiformis Honda 'Giganteus'," *Plant Cell, Tissue and Organ Culture* 45:43-52 (1996).

Holme et al., "Embryogenic Callus Formation, Growth and Regeneration in Callus and Suspension Cultures of *Miscanthus* x Olgiformis Honda 'Giganteus' as Affected by Proline," *Plant Cell, Tissue and Organic Culture* 50:203-210 (1997).

Holme, "Growth Characteristic and Nutrient Depletion of *Miscanthus* x Ogiformis Honda 'Giganteus' Suspension Cultures," *Plant Cell, Tissue and Organ Culture* 53:143-151 (1998).

Lester et al., "Somatic Embryogenesis and Genetic Transformation in *Arundo donax* L.," *World Congress on in vitro Biology* Abstract E-2006 (2004).

Lewandowski et al., "Possibilities for the Establishment of an in-vitro-propagation System for *Miscanthus* "Giganteus" by Using Different Parts of the Plant as Donor Tissue," *Bodenkultur* 44:243-252 (1993), Engl Abst only.

Linder et al., "Tissue Culture and Regeneration of the Giant Reed, *Arundo donax* L.," *American Journal of Botany* 85:Abstract 257, p. 89 (1998).

Singh et al., "Plant Regeneration of *Arundo donax* L. Through Somatic Embryogenesis," Meeting for the Society for In Vitro Biology, Jun. 25-29, 2002, Orlando, FL, *In Vitro Cell. Dev. Biol.* 39: Abstract p. 2062.

Toth et al., "Embryotic Callus Induction of Different Explants of *Miscanthus sinensis, Miscanthus* x *giganteus* and *Arundo donax* Genotypes," in Sustainable Agriculture for Food, Energy and Industry pp. 249-253, N. El Bassam, ed., James & James Science Publishers, London (1998).

Toth et al., "In-vitro Cultures of Different Explants of *Miscanthus sinensis, Miscanthus* x *giganteus* and *Arundo donax* Genotypes," *Proceedings of the 10th European Conference for Biomass for Energy and Industry*, Würzburg, Germany, Jun. 1998, pp. 1062-1066.

Toth et al., "Nutrient Uptake of *Miscanthus* in vitro Cultures," *Journal of Natural Fibers* 3:1-2 (2006).

International Search Report and Written Opinion of International Application No. PCT/US2007/011008 mailed Apr. 9, 2008. (21 pages).

Buyukalaca et al. "A Novel Method for Separation of Somatic Embryos from Embroygenic Suspension Cultures by Cold Treatment" *J. Plant Biochem. & Biotech.* 12:143-146 (2003).

Communication Relating to the Results of the Partial International Search for International Application No. PCT/US2007/011008 on Jan. 23, 2008 (5 pages).

Czako et al. "Genetic Modification of Wetland Grasses for Phytoremediation" *Z. Naturforsch* 60c:285-291 (2005).

Kuiper et al. "Selection of a Plant-Bacterium Pair as a Novel Tool for Rhizostimulation of Polycyclic Aromatic Hydrocarbon-Degrading Bacteria" *MPMI* 14(10):1197-1205 (2001).

Liu. "Factors Affecting Induction, Somatic Embryogenesis and Plant Regeneration of Callus from Cultured Immature Inflorescences of Sugarcane" *J. Plant Physio.* 141:714-720 (1993).

Ma et al. "Comparison of Anther and Microspore Culture in the Embryogenesis and Regeneration of Rye (*Secale cereale*)" *Plant Cell, Tissue and Organ Culture* 76:147-157 (2004).

Malabadi et al. "Cold-Enhanced Somatic Embryogenesis in *Pinus patula* is Mediated by Calcium" *South African J. of Botany* 72:613-618 (2006).

Reidiboym-Talleux et al. "Improvement of Somatic Embryogenesius in Wild Cherry (*Prunus avium*). Effect of Maltose and ABA Supplements" *Plant Cell, Tissue and Organ Culture* 55:199-209 (1999).

Shariatpanahi et al. "Stresses Applied for the Re-programming of Plant Microspores Towards in vitro Embryogenesis" *Physiol. Plantarum* 127:519-534 (2006).

Singh et al. "Expression of GFP Reporter Gene in *Arundo donax* Following Microprojectile Bombardment" *In Vitro Cell. Dev. Biol.* 39: Abstract p. 2018 (2003).

Sticklen et al. "Invited Review: Shoot Apical Meristem: A Sustainable Explant for Genetic Transformation of Cereal Crops" *In Vitro Cell. Dev. Biol.—Plant* 41:187-200 (2005).

Wang et al. "Plant Regeneration Via Somatic Embryogenesis in the Brackish Wetland Monocot *Scirpus robustus*" *Aquatic Botany* 79:163-174 (2004).

Xiao-Yan et al. "Production and Analysis of Transgenic Maize with Improved Salt Tolerance by the Introduction of *AtNHX1* Gene" *Acta Botanica Sinica* 46(7):854-861 (2004).

Zhang et al. "Transformation of Recalcitrant Maize Elite Inbreds Using in vitro Shoot Meristematic Cultures Induced from Germinated Seedlings" *Plant Cell Rep.* 21:263-270 (2002).

\* cited by examiner

METHOD FOR MICROPROPAGATION OF MONOCOTS BASED ON SUSTAINED TOTIPOTENT CELL CULTURES

STATEMENT OF GOVERNMENT SUPPORT

The present invention was funded in part by government support under grant number 10049180 from the National Institutes of Health. The United States Government has certain rights in this invention.

FIELD OF THE INVENTION

The present invention relates to novel methods for large-scale micropropagation of plants of the Class Monocotyledoneae.

BACKGROUND OF THE INVENTION

Plant regeneration from cultured cells of the great majority of monocot (mostly graminaceous) species that have been reported so far, is achieved from callus initiated on high concentrations of a strong auxin, such as 2,4-dichlorophenoxyacetic acid (2,4-D) (Conger, B. V. et al., *Current Issues in Plant Molecular and Cellular Biology*, pp. 59-68 (1995)). The synthetic auxin, 2,4-D, is considered to be the best plant hormone to induce embryogenic callus. Embryogenic callus is typically obtained from monocots by inducing the primary cell culture on a medium containing one or more auxin-type plant hormones followed by a secondary cultivation step on a lowered auxin but in the presence of a cytokinin-type plant hormone. The embryogenic potential of monocot cell cultures diminishes over time, making it necessary to reinitiate the primary cell culture (U.S. Pat. No. 6,153,812 issued Nov. 28, 2000; Trigiano and Gray, *Plant tissue culture concepts and laboratory exercises*. Second ed., Boca Raton: CRC Press (2000)).

Plants from the Class Monocotyledoneae are often multi-purpose plants. Giant reed, *Arundo donax*, for example, has been used for 5,000 years for pipe instruments and is the source for reeds for clarinets and organ pipes. Even with today's modern technology, most of the reeds for woodwind musical instruments are still made from *A. donax* culms.

Giant reed is also used for erosion control and has great potential for use as an energy crop (Szabo, P., et al., *J. Anal. Appl. Pyrolysis*, 36:179-190 (1996)). The culms are also used for fishing rods, walking sticks, mats and lattices in the construction of adobe huts. Giant reed is also a source of industrial cellulose for paper and rayon making, and for the production of other polysaccharides (Neto, C. P. e al., *Ind. Crops & Prods.*, 6:51-58 (1997). It has even been considered as a source of pulp for the making of paper. Additionally, giant reed can also be used in bioremediation efforts to remove environmental pollutants from water and land areas.

Giant reed is only one of many monocots that exhibit such multiple uses. Whether used as ornamentals, sources of energy, or as useful vehicles to carry out industrial processes, such grass-like plants are important.

The present inventors have found that 2,4-D induced callus cultures obtained from giant reed nodal segments and segments of immature inflorescences fail to produce sustained embryogenic cell cultures and embryos even upon transfer to low auxin or no auxin in combination with a cytokinin, as is the typical practice (U.S. Pat. No. 6,153,812 issued Nov. 28, 2000; Trigiano and Gray, *Plant tissue culture concepts and laboratory exercises*. Second ed., Boca Raton: CRC Press (2000)). The finding that these methods fail to produce embryogenic cultures is corroborated by Tóth and Mix-Wagner and Linder and Gallagher where Tóth and Mix-Wagner reported the formation of callus that was claimed to be embryogenic but they failed to obtain embryos and plant regeneration and Linder and Gallagher announced one-time plant regeneration from callus without the potential for mass propagation (Tóth and Mix-Wagner, *Sustainable agriculture for food, energy and industry: strategies towards achievement: proceedings of the international conference held in Braunschweig, Germany*, June 1997, N. El Bassam, et al., Eds., James & James (Science Publishers) Ltd.: London. pp. 249-253 (1998); Linder and Gallagher, Abstract No. 257, *American Journal of Botany*, 85(6): 89 (1998)).

Accordingly, it would be useful to have methods for the large-scale micropropagation and macropropagation of *Arundo donax* and other monocot plants. Thus, the present invention provides a comprehensive set of methods for the production, propagation, maintenance, storage, transportation and deployment of sustained embryogenic cell cultures as well as derived secondary and tertiary totipotent tissue cultures from plant species of the Class Monocotyledoneae and from elite plant lines derived therefrom. The plant micropropagation technology of the present invention based on the sustained embryogenic cultures provides unprecedented efficiency.

SUMMARY OF THE INVENTION

The present invention provides a comprehensive set of methods for the initiation, mass micropropagation, maintenance, storage, transportation, and/or for deployment of propagules. The present invention further provides methods for enhanced somaclonal breeding of monocotyledous plant species utilizing the sustained embryogenic cell culture induction and maintenance technology described herein. The methods of the present invention can thus provide superior plant clones in commercially viable numbers at an industrial scale that can be used for many purposes including remediation and biomass plantations. Thus, the present invention further provides methods for industrial scale, cost effective, mass production of field ready propagules for the production of monocot plants using multiple or a single subculture technology from embryogenic cell cultures.

Accordingly, one embodiment of the present invention is a method of producing and maintaining a totipotent embryogenic cell culture of a monocotyledonous plant comprising: (a) cultivating an explant of tissue from a monocotyledonous plant shoot tip on a primary medium, wherein the explant has been pretreated with a cold temperature and the primary medium comprises auxin or auxin and cytokinin, to produce a totipotent embryogenic cell culture; (b) treating the totipotent embryonic cell culture with a cold temperature; and c) maintaining the totipotent embryogenic cell culture by further cultivation on the primary medium and/or on a secondary medium, whereby a totipotent embryogenic cell culture of a monocotyledonous plant is produced and maintained.

A further embodiment provides a method of micropropagating a monocotyledonous plant comprising: (a) cultivating an explant of tissue from a monocotyledonous plant shoot tip on a primary medium, wherein the explant has been pretreated with a cold temperature and the primary medium comprises auxin or auxin and cytokinin, to produce a totipotent embryonic cell culture; (b) treating the totipotent embryonic cell culture with a cold temperature; (c) maintaining the totipotent embryogenic cell culture by cultivation on a secondary medium, whereby a totipotent embryogenic cell culture of a monocotyledonous plant is produced and maintained; and (d) transferring the embryogenic cell culture of step (c) to a tertiary medium to continue multiplication and to produce a plantlet with roots and shoots, thereby micropropagating a monocotyledonous plant.

In still further embodiments, a method of micropropagating a monocotyledonous plant is provided comprising: (a) cultivating an explant of tissue from a monocotyledonous plant shoot tip on a primary medium, wherein the explant has been pretreated with a cold temperature and the primary medium comprises auxin or auxin and cytokinin, to produce a totipotent embryogenic cell culture; (b) treating the totipotent embryonic cell culture with a cold temperature; (c) maintaining the totipotent embryogenic cell culture by cultivation on a secondary medium, whereby a totipotent embryogenic cell culture of a monocotyledonous plant is produced and maintained; (d) transferring the embryogenic cell culture of step (c) to a tertiary medium to continue multiplication and to produce a plantlet with roots and shoots; and (e) transferring the plantlet to a quaternary medium for acclimatization to non-sterile and photosynthetic conditions and production of an acclimatized plantlet or plant.

Another embodiment of the present invention provides a method of producing an elite plant line comprising: selecting for at least one trait of interest in the totipotent embryogenic cell culture and/or plantlet produced by the methods of the present invention, wherein the at least one trait of interest is a result of somaclonal variation in the embryogenic cell culture or the introduction of at least one heterologous nucleotide sequence into the genome of a cell of the embryogenic cell culture; and cultivating the totipotent embryogenic cell culture comprising the at least one trait of interest to produce an elite plant line.

A further embodiment provides a method wherein a plant-microbe association is established, the method comprising co-cultivating at least one plantlet produced by the methods of the present invention with at least one microbial species in a quaternary medium to establish a plant-microbe association.

The present invention additionally provides methods directed to phytoremediation. In one embodiment, the phytoremediation comprises establishing a plurality of plants produced by methods of the present invention and possessing the same genetic characteristics in a liquid medium, and contacting the roots of the plants with an environmental pollutant in the liquid medium, thereby causing the environmental pollutant to be removed from the liquid medium.

In other embodiments, phytoremediation comprises establishing a plurality of plants produced by methods of the present invention and possessing the same genetic characteristics in a land area and contacting the roots of the plants with an environmental pollutant in the land area, thereby causing the environmental pollutant to be removed from the land area.

Still further embodiments of the present invention include a totipotent tissue or a transgenic totipotent tissue of a monocot plant that is produced by the methods described herein.

BRIEF DESCRIPTION OF THE FIGURES

FIG. 1A shows the first step in embryogenesis on secondary culture medium, asymmetric cell division; FIG. 1B shows the highly cytoplasmic, actively dividing cells in embryogenic cell culture on secondary culture medium; and FIGS. 1C and 1D show nonzygotic embryo from cell culture on secondary culture medium.

FIG. 3A shows the formation of embryogenic cell culture on immature inflorescence segments; FIG. 3B shows sustained totipotent embryogenic cell culture on secondary culture medium; FIG. 3C shows unipolar nonzygotic embryos forming on the sustained totipotent embryogenic cell culture on secondary culture medium; FIG. 3D shows plants regenerated from the embryogenic cell culture and multiplying in liquid tertiary culture medium; FIG. 3E shows plants transferred to pots from the quaternary culture medium; and FIG. 3F shows a three-month-old stand of *A. donax* established from in vitro cloned plants.

FIG. 4A and 4B show sustained totipotent embryogenic cell culture on secondary culture medium; FIG. 4C and 4D show plants regenerating from the embryogenic cell culture on tertiary culture medium in the dark; and FIG. 4E shows plants in liquid tertiary culture medium under light.

FIG. 5A. *Miscanthus floridulus* in the secondary cultivation stage; FIG. 5B. *Thysanolaena maxima* in the secondary cultivation stage; FIG. 5C *Scirpus validus* in the acclimatization stage; FIG. 5D *Scirpus californicus* in the tertiary cultivation stage.

FIG. 6A shows control explants killed by 10 mg/L of phosphinothricin (antibiotic/herbicide); FIG. 6B shows the development of embryogenic callus in the absence of the antibiotic/herbicide in the case of the control explants; FIG. 6C shows that co-cultivated antibiotic resistant transformed explants are able to develop embryogenic callus in the presence of 10 mg/L of phosphinothricin; and FIG. 6D shows the development of embryogenic callus in the case of cocultivated antibiotic resistant transformed explants in the absence of the antibiotic/herbicide.

FIG. 7A shows the dispersion of vegetative clones, obtained by conventional nursery propagation, with respect to dehalogenase activity; FIG. 7B shows the dispersion of somaclones obtained from embryogenic cell cultures; FIG. 7C shows the dispersion of somaclones obtained from embryogenic cell cultures exposed to TCP; and FIG. 7D presents the data charted as quartiles.

DETAILED DESCRIPTION

Figure 1:
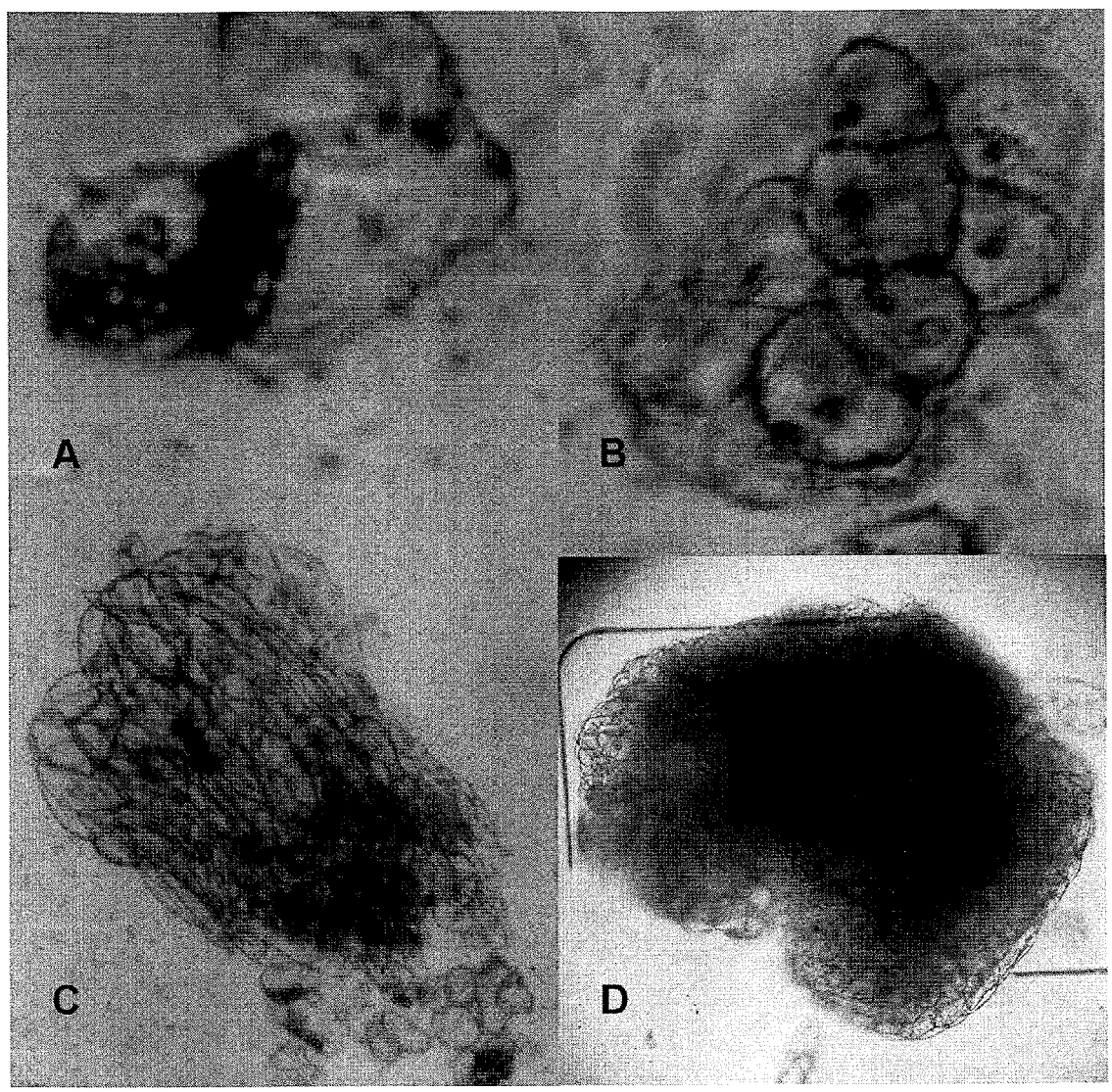
FIG. 1 shows sustained totipotent embryogenic cell culture of *Arundo donax*.

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the claims set forth herein, the singular forms "a," "an," and "the" are intended to include the plural forms as well, unless the context clearly indicates otherwise. As used herein, the term "and/or" includes any and all combinations of one or more of the associated listed items.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

All publications, patent applications, patents and other references cited herein are incorporated by reference in their entireties for the teachings relevant to the sentence and/or paragraph in which the reference is presented.

Definitions.

As used herein "auxin" refers to any compound with auxin or auxin-like activity. "Auxin-like activity" refers to the typical activity observed in a plant as a result of treatment with auxin. Thus, a compound with auxin-like activity promotes the formation of unorganized cell mass on explants, maintains cell proliferation alone or in the presence of cytokinin and/or induces root development on shoot cuttings.

As used herein "cold pretreatment" refers to the cold treatment of explants prior to introduction into cell culture.

As used herein "cold treatment" refers to incubation of the established embryogenic cell cultures in the cold.

As used herein "cytokinin" refers to any compound with cytokinin or cytokinin-like activity. "Cytokinin-like activity" refers to the typical activity observed in a plant as a result of treatment with cytokinin. Thus, a compound with cytokinin-like activity promotes shoot regeneration from cell cultures and/or maintains cell proliferation in the presence of auxin.

Embryo is defined as the earliest recognizable multicellular stage of an individual.

"Embryogenic cultures" as used herein refers to cultures that can produce somatic embryos or embryo derived structures, which are able to further differentiate and form a plantlet.

As used herein, the phrase "increased tolerance to an environmental condition" means the ability of a plant to withstand a deleterious environmental condition that would normally be harmful or deleterious to a wild-type plant of the same species.

"Plantlet" as used herein refers to a young or small plant with roots and shoots. In some embodiments of the present invention, the plantlets are 0.5-10 cm in height.

"Primary totipotent embryogenic cell culture" as used herein refers to a non-organized mass of actively dividing undifferentiated cells which are able to differentiate into non-zygotic embryogenic structures, embryos and embryo derived structures which can further differentiate and form a plantlets.

"Propagule" as used herein refers to plants and plantlets that are used for propagating a plant and are ready to be transplanted into soil or other planting medium.

"Rehabilitate" or "rehabilitation" and other like terms as used herein refer to transferring of the cultures, which have been in storage, to fresh medium.

As used herein, the term "subculture," or "passage" refers to the transfer of cells from one culture vessel to another; this usually involves the subdivision of a proliferating cell culture. Thus, "subculture" is the process by which the tissue or explant is subdivided and then transferred into fresh culture medium.

"Sustained totipotent embryogenic cell culture" as used herein refers to a mixture of non-organized actively dividing undifferentiated cells and cells differentiating into nonzygotic embryogenic structures, embryos and embryo derived structures, which can further differentiate and form plantlets for years.

As used herein "totipotent" means having unlimited capability to produce any type of cell. Totipotent cells have the capability to turn (or "specialize") into any and all of the tissues and organs that are present in the completely developed plant. Thus, totipotent cells have the capability to regenerate into whole plants.

As used herein "xenobiotic" refers to a chemical or other compound which is not a normal component of an organism which is exposed to it; a chemical that is foreign to the biological system.

It will be understood that, although the terms "primary", "secondary", etc. may be used herein to describe various cultivation steps and/or media, these cultivation steps and/or media should not be limited by these terms. These terms are only used to distinguish one cultivation step or media from another cultivation step or media. Thus, a "primary" cultivation step or media, discussed below could also be termed a "secondary" cultivation step or media without departing from the teachings of the present invention.

The present invention provides new methods for the initiation, mass micropropagation, maintenance, storage, transportation and/or deployment of propagules as well as for enhanced somaclonal breeding of select plant species. In representative embodiments, the present invention further provides plant clones in commercially viable numbers at an industrial scale for among other uses, remediation and biomass plantations. These methods utilize a sustained embryogenic cell culture induction and maintenance technology that to the inventors' knowledge provides the first sustained embryogenic cell culture of such monocots as giant reed, tigergrass, *Miscanthus* and bulrush species.

The sustained embryogenic cell culture utilized by the presented methods is unlimitedly totipotent. During proliferation, each cell is a unit of multiplication and can undergo embryogenesis independently allowing cellular level selection for differential growth under selective conditions. In contrast, in cultures where somatic embryos or multiple shoot primordia are induced directly from an explant in a suspension or in a semi-solid secondary culture (e.g., U.S. Pat. No. 7,052,912 (hereinafter "the '912 patent")) the totipotent unit number is very limited (i.e., the number of individuals) as compared to the totipotent embryogenic cell culture of the present invention where every cell is a potential individual. In the '912 patent, the multiplication, which is generated from secondary formation of embryos or adventitious shoot meristems comprising hundreds or thousands of cells, is limited to a much lower rate because the individual plants regenerated are not originated at the cellular level from individual cells. This not only affects the number of potential individual plants but also the efficiency of sorting out of novel or elite lines for breeding.

The embryogenic cell culture induction methods of the present invention were developed for a diverse group of monocot species, including *Arundo donax*. The method is based in part on the present inventors' discovery of the embryogenic growth inducing effect of cold pre-treatment of shoot tips containing immature inflorescences. While not wishing to be bound by any particular theory of the invention, it appears that the cold pretreatment not only induces physiological changes that cause the retention and increase of competence for induction of embryogenic cell cultures but also delays senescence and opens a wider window for processing the plant material. The invention is further based on the unexpected discovery that the transfer from media providing a combination of auxins and cytokinins to a media providing only cytokinin, such as the synthetic cytokinin, thidiazuron, results in the promotion of shoot elongation and root formation.

The sustained embryogenic cell culture of the present invention is composed of dividing cells which can produce unipolar embryos. In the presence of light, the unipolar embryos germinate precociously and form multiple shoot apical meristems and shoot primordia. On tertiary medium, the partial elongation of the shoots is accompanied by rooting. Thus, the methods of the present invention are suitable for not only for sustained maintenance and micropropagation of the totipotent cell culture lines but also for maintenance of sustained regenerating tissue culture lines as well.

Initiation and Production.

The present invention provides a method of producing and maintaining a totipotent embryogenic cell culture of a monocotyledonous plant comprising: (a) cultivating an explant of tissue from a monocotyledonous plant shoot tip on a primary medium, wherein the explant has been pretreated with a cold temperature and the primary medium comprises auxin or auxin and cytokinin, to produce a totipotent embryogenic cell culture; (b) treating the totipotent embryonic cell culture with a cold temperature; and (c) maintaining the totipotent embryogenic cell culture by further cultivation on the primary medium and/or on a secondary medium, whereby a totipotent embryogenic cell culture of a monocotyledonous plant is produced and maintained.

In some embodiments, the totipotent cell culture that is generated in the primary cultivation step is maintained on the same medium and under the same conditions in order to continue the generation of totipotent tissue. In other embodiments, the totipotent cell culture that is generated in the primary cultivation step is transferred to a secondary medium for sustained proliferation of the totipotent cell culture. Examples of growth of *A. donax* on secondary culture medium are provided in FIG. 1.

Figure 2:
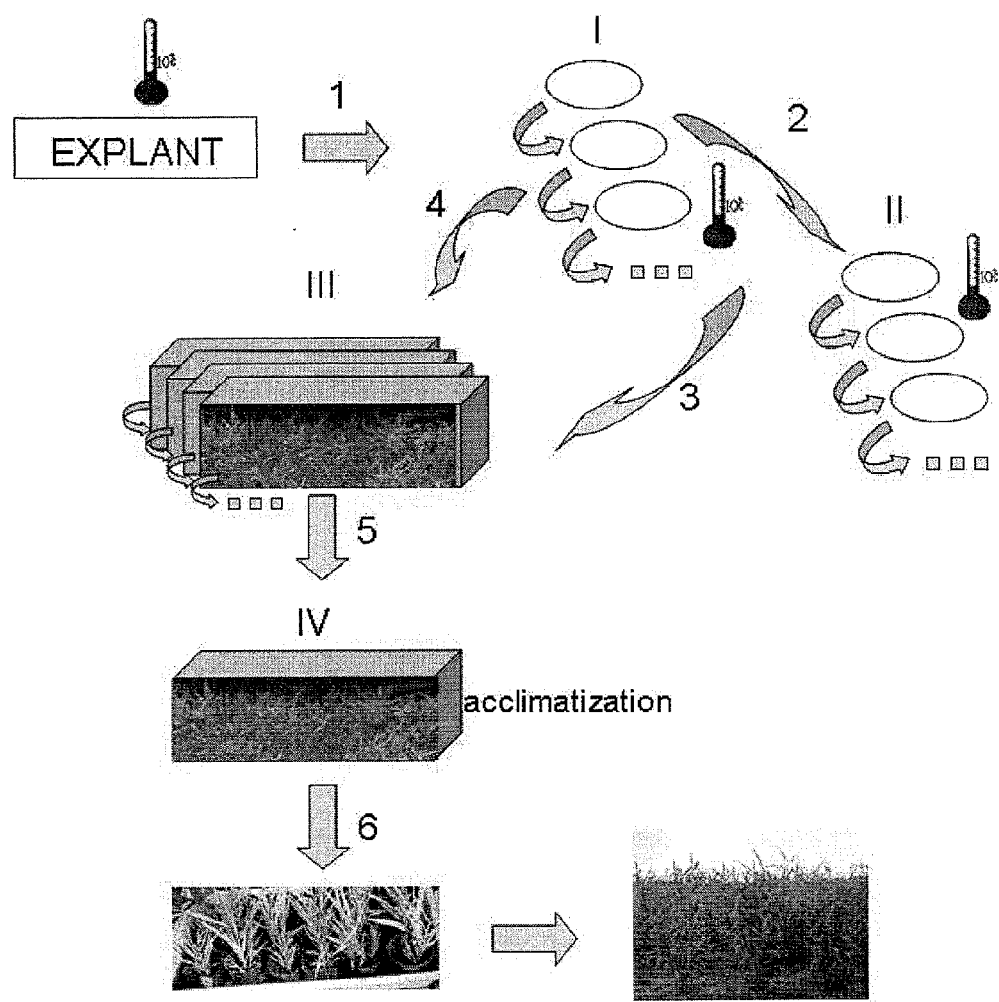
FIG. 2 shows the stages of industrial scale propagation. Step 1 is the initiation of the embryogenic cell culture on primary cultivation medium (I). The embryogenic cell culture can be propagated on primary culture medium with or without intermittent cold treatment. Step 2 is the transfer to secondary culture medium (II) where the cell culture can be propagated with or without intermittent cold-treatment. Step 3 shows the transfer from secondary to tertiary culture medium (III). Step 4 illustrates an alternative route wherein the cell culture from the primary cultivation medium is transferred directly to the quaternary cultivation medium (IV). Step 5 is acclimatization of the cultures on the quaternary cultivation medium. Step 6 is the transfer of the plants into soil.

In further embodiments, the totipotent cell culture is subjected to cold treatment on secondary medium in order to increase growth rate. In another aspect of the invention, a method of micropropagating a monocot plant is provided wherein the totipotent cell culture is transferred from secondary medium to tertiary medium and allowed to form partially elongated shoots with roots (plantlets). The resulting plantlets can be cultivated further on a quaternary medium free of hormones, vitamins and sugars for further growth and acclimatization to non-sterile and photosynthetic conditions, thereby producing an acclimatized plantlet or plant. The plantlets can be transferred from the quaternary medium to soil for further acclimatization. Alternatively, the plantlets can be transferred directly to soil from the tertiary medium in order to produce an acclimatized plantlet or plant of the present invention. Following acclimatization, the plantlets or plants can be transplanted to any desired location. A representative embodiment of the micropropagation methods of the present invention is presented in FIG. 2.

The shoot tip of the present invention includes, but is not limited to, an inflorescence, an immature inflorescence and an immature infructescence comprising immature to mature flowers and immature fruits. The explant or shoot tip of living tissue from a monocot plant can be obtained from any source, including, but not limited to, wild monocot plants, cultivated monocot plants (greenhouse and field grown), and monocot plants regenerated from explants using the methods of the present invention. A monocotyledonous plant of the present invention includes, but is not limited to, *Arundo* spp., *Thysanolaena* spp., *Miscanthus* spp., and *Scirpus* spp., and combinations thereof. Thus, a monocotyledonous plant of the present invention includes, but is not limited to, giant reed (*Arundo donax*), tigergrass (*Thysanolaena maxima*), the silvergrasses (*Miscanthus* x *giganteus* and *Miscanthus floridulus*), and the bulrushes (*Scirpus californicus* and *Scirpus validus*).

In the case of monocots of the grass family, in particular, giant reed (*Arundo donax*), tigergrass (*Thysanolaena maxima*), and the silvergrasses (*Miscanthus* x *giganteus* and *Miscanthus floridulus*), the explant can be an immature inflorescence. In one particular embodiment, the explant is obtained from the tips of preflowering shoots with leaf sheaths completely enclosing the developing, but yet unemerged immature inflorescence. In particular embodiments, an immature inflorescence enclosed in leaf sheaths exhibits a higher yield of regenerable tissue than other grass tissue sources.

An explant obtained from a living bulrush plant, in particular, *Scirpus californicus* and *Scirpus validus*, is obtained, for example, from the shoots early in flowering (e.g., without open flowers or mostly with unopened flowers, open flowers and developing fruits; also referred to as an immature inflorescence or infructescence). In the case of bulrush, in particular embodiments, the immature inflorescence or infructescence exhibits a higher yield of regenerable tissue than other bulrush tissue sources.

In an exemplary method of preparing the explant of a living monocot plant of the grass family for cultivation, in particular giant reed or the silvergrasses, all but the terminal leaf sheaths are carefully stripped so as not to expose the inflorescence. In an exemplary method of preparing the explant of a living monocot plant of the bulrush type for cultivation, in particular *Scirpus californicus* and *Scirpus validus*, the branches of the inflorescence or the infructescence are cut off. Other methods of preparing explants will be apparent to those skilled in the art.

The shoot tips of the grasses and the bulrushes can be sanitized, or surface sterilized. One exemplary method of surface sterilization is immersion of the shoot tips in a solution of 5 times diluted commercial bleach containing 10% v/v ethanol and a surfactant, for example, 0.1% Tween 80, for 15 minutes. The shoot tips are then rinsed three times with sterile water prior to further use. Such sterilization reduces or eliminates environmental microbial contamination. The inflorescence of the grass is then excised away from all leaf sheaths under aseptic conditions and is cut or chopped into cross-sectional pieces. Following sterilization, the inflorescence of the bulrush is cut or chopped into cross-sectional pieces under aseptic conditions. Any sterilized sharp blade, knife, or scalpel can be used for the cutting of the inflorescence. By cutting an aseptic immature inflorescence containing a number of meristematic regions into cross-sectional pieces, the formation of regenerable tissue is induced.

In some embodiments, the explants are pretreated with a cold temperature. Such a cold pretreatment of the explant can result in a higher yield of regenerable tissue than those explants that are used immediately after excising or those that are stored at ambient temperature. The duration of the cold pretreatment can be from about 1 day to about 120 days. Thus, the cold treatment can be one day, one week, two weeks, three weeks, one month, two months, three months and four months and the like. In further embodiments, the cold pretreatment can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99, 100, 105, 110, 115, or 120 days and the like. Accordingly, the cold pretreatment can be from about one day to about 14 days, one day to about 30 days, one day to about 45 days, one day to about 60 days, one day to about 90 days, or one day to about 105 days, and the like. In other embodiments, the cold pretreatment can be from about 7 days to about 14 days, about 7 days to about 30 days, about 14 days to about 30 days, about 14 days to about 45 days, about 14 days to about 60 days, about 30 days to about 45 days, about 30 days to about 60 days, about 30 days to about 90 days, about 45 days to about 60 days, about 45 days to about 90 days, about 45 days to about 120 days, about 60 days to about 90 days, 60 days to about 120 days, or about 90 days to about 120 days, about 90 days to about 180 days, and the like. In a particular embodiment, the cold pretreatment is a duration of 14 days (two weeks).

In representative embodiments, the pretreatment temperature can be in a range from about 0° C. to about 10° C. Thus, the pretreatment temperature can be about 0° C., 1° C., 2° C., 3° C., 4° C., 5° C., 6° C., 7° C., 8° C., 9° C., or 10° C. or any combination thereof. In other embodiments, the pretreatment temperature can be in a range from 0° C. to about 5° C., from about 0° C. to about 8° C., from about 2° C. to about 10° C., from about 2° C. to about 8° C., from about 2° C. to about 5° C., from about 3° C. to about 5° C., from about 3° C. to about 7° C., from about 3° C. to about 10° C., from about 5° C. to about 8° C., from about 5° C. to about 10° C., or from about 7° C. to about 10° C., from about 8° C. to about 10° C., and the like. In a further embodiment, the pretreatment temperature is 5° C. In some embodiments, the pretreatment at a cold temperature is done in the presence of light. In a specific embodiment, the pretreatment is done in the presence of dim light. Dim light as used herein is a light intensity of less than 30 micromoles m$^{-2}$ s$^{-1}$.

In particular embodiments, the pieces of the cut-up inflorescence or infructescence are cultivated in a primary cultivation step in which totipotent tissue is generated. In some embodiments, the primary cultivation is carried out in the dark and, optimally, at approximately room temperature. In other embodiments, the primary cultivation step is carried out in the light and at approximately room temperature. The inventors have found that the cultures exhibit increased multiplication rates and increased longevity when maintained in the dark over those cultures maintained in the light.

The primary cultivation step can be carried out for any period of time and at any temperature sufficient to generate the totipotent embryogenic tissue culture. In representative embodiments, the duration of the primary cultivation step is from about one week to several months. Thus, the duration of the primary cultivation step can be about one week, two weeks, three weeks, one month, two months, three months and four months and the like. In some embodiments the duration of the primary cultivation step is about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99, 100, 105, 110, 115, or 120 days and the like. In one embodiment, the duration of the primary cultivation is about four weeks. In still further embodiments the duration of the primary cultivation step is about one week to about three weeks, about one week to about four weeks, about one week to about five weeks, about one week to about six weeks, about one week to about seven weeks, about one week to about eight weeks, about one week to about ten weeks, about one week to about twelve weeks, about one week to about fourteen weeks or about one week to about sixteen weeks, one week to about eighteen weeks, and the like.

The temperature for the primary cultivation step is not critical and can be any temperature suitable for producing a totipotent embryogenic cell culture. Accordingly, the temperature for the primary cultivation step can be in a range from about 15° C. to about 35° C. Thus, the temperature for the primary cultivation step is about 15° C., 16° C., 17° C., 18° C. 19° C., 20° C., 21° C., 22° C., 23° C., 24° C., 25° C., 26° C., 27° C., 28° C., 29° C., 30° C., 31° C., 32° C., 33° C., 34° C., 35° C., or any combination thereof. In some embodiments, the temperature range for the primary cultivation step is about 15° C. to about 20° C., about 15° C. to about 25° C., about 15° C. to about 30° C., about 20° C. to about 25° C., about 20° C. to about 30° C., about 20° C. to about 35° C. or about 25° C. to about 30° C., and the like. In a further embodiment, the temperature range for the primary cultivation step is about 26° C. to about 28° C. In a still further embodiment, the temperature range for the primary cultivation step is about 25° C.

The present invention additionally provides a method of treating a totipotent embryogenic cell culture with a cold temperature, the method comprising incubating the totipotent embryogenic cell culture of step (a) of claim 1 and exposing the cell culture to at least one cold treatment. In representative embodiments, the totipotent cell cultures of step (a) are incubated in individually sealed culture dishes. Culture dishes of the present invention include any type of dish, flask and/or bottle and the like in which tissue culture cells can be grown. These include, but are not limited to, Petri dishes, tissue culture flasks, Erlenmeyer flasks, microtiter plates and multiple-well cell culture plates. In some embodiments, the culture dishes can be sealed using sealants including, but not limited to, food service film, parafilm, pallet wrap and the like.

In some embodiments, the treating of the totipotent embryogenic cell culture with a cold temperature occurs in the dark. In other embodiments, the cold treatment can occur in the light or with intermittent light. The intensity of light can be dim (less than 30 micromoles m$^{-2}$ s$^{-1}$). As one of ordinary skill in the art would understand, even in the dark grown cultures, exposure to light is possible when the cultures are subcultured or otherwise handled.

In other aspects of the present invention, treating with a cold temperature comprises treatment at a temperature in a range from about 4° C. to about 10° C., about 4° C. to about 8° C., about 4° C. to about 6° C., about 5° C. to about 8° C., about 5° C. to about 10° C., about 6° C. to about 10° C., about 6° C. to about 8° C., about 7° C. to about 10° C., about 8° C. to about 10° C., and the like. Thus, the cold treatment comprises treatment at a temperature of about 4° C., 5° C., 6° C., 7° C., 8° C., 9° C., 10° C., or any combination thereof.

The duration of the cold treatment can be about 1 to about 300 days, or more. Thus, the duration of the cold treatment can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99, 100, 105, 110, 115, 120, 125, 130, 135, 140, 145, 150, 160, 170, 180, 190, 200, 210, 220, 230, 240, 250, 260, 270, 280, 290, 300 days, 310 days, 320 days, 330 days, 340 days, 350 days, 360 days, or any combination thereof. In one embodiment, the duration of the cold treatment can be about 5 days to about 90 days. In other embodiments, duration of the cold treatment can be about 5 days to about 15 days, about 5 days to about 30 days, about 5 days to about 45 days, about 5 days to about 105 days, about 5 days to about 120 days, about 5 days to about 150 days, about 5 days to about 175 days, about 5 days to about 200 days, about 5 days to about 225 days, about 5 days to about 250 days, about 5 days to about 275 days, about 5 days to about 300 days, about 15 days to about 30 days, about 15 days to about 45 days, about 15 days to about 90 days, about 15 days to about 120 days, about 15 days to about 150 days, about 15 days to about 175 days, about 15 days to about 200 days, about 15 days to about 250 days, about 15 days to about 300 days, about 30 days to about 45 days, about 30 days to about 90 days, about 30 days to about 120 days, about 30 days to about 150 days, about 30 days to about 175 days, about 30 days to about 200 days, about 30 days to about 225 days, about 30 days to about 250 days, about 30 days to about 275 days, about 30 days to about 300 days, about 30 days to about 325 days, about 45 days to about 60 days, about 45 days to about 90 days, about 45 days to about 120 days, about 45 days to about 150 days, about 45 days to about 200 days, about 45 days to about 250 days, about 45 days to about 300 days, about 45 days to about 320 days, about 90 days to about 120 days, about 90 days to about 150 days, about 90 days to about 175 days, about 90 days to about 200 days, about 90 days to about 220 days, about 90 days to about 250 days, about 90 days to about 300 days, about 90 days to about 350 days, about 90 days to about 350 days, about 120 days to about 180 days, about 120 days to about 250 days, about 120 days to about 350 days, about 180 days to about 250 days, or about 180 days to about 350 days, and the like.

In additional embodiments, the totipotent embryogenic cell culture is treated with a cold temperature for up to 180 days without subculture. In a further embodiment, the totipotent embryogenic cell culture is treated with a cold temperature for up to 180 days with at least one subculture.

The cold treatments of the explants and the established cultures were unexpectedly found to result in an increased growth rate of the embryogenic cell mass with a multiplication rate of 5× to 8× as compared to the 2× to 3× observed without the cold treatment. This dramatic increase of efficiency is of commercial significance since most industrial scale operations are limited by the multiplication rate. The observed positive effect of the cold treatments was a particularly surprising finding since many of the plants of the present invention are cold sensitive species.

A medium that is useful for the primary cultivation step (i.e., the primary medium) can be any basal medium used for plant tissue culture. Such media are well known to those of skill in the art. In one embodiment, the primary medium is supplemented with at least one plant hormone (i.e., plant growth regulator). Examples of suitable plant hormones include auxins and cytokinins. Auxins of the present invention include not only auxin but also any compound with auxin-like activity. Thus, auxins of the present invention include, but are not limited to, 2,4-dichlorophenoxyacetic acid, picloram, and indolebutyric acid and combinations thereof. Cytokinins of the present invention include not only cytokinin but also any compound with cytokinin-like activity. Thus, cytokinins of the present invention include, but are not limited to, thidiazuron, zeatin, benzyladenine, kinetin, adenine hemisulfate and dimethylallyladenine, and combinations thereof. In some embodiments, the primary medium is supplemented with at least one auxin and at least one cytokinin.

In representative embodiments, the primary medium also comprises a carbon source, which can be any carbon source appropriate for plant tissue culture. Such carbon sources are known to those of ordinary skill in the art (Slater et al. *Plant Biotechnology, the Genetic Manipulation of Plants*, Oxford University Press, 368 pp., (2003)) and include, but are not limited to, sugars such as sucrose, glucose, maltose, galactose and sorbitol, and the like. In the present invention, the preferred carbon source is sucrose.

In one embodiment of the present invention, the primary medium is prepared by adding to sterile water: (a) MS (Murashige and Skoog, 1975) basal salts (Sigma Fine Chemicals, St. Louis, Mo.), 4.3 g/l; (b) Miller's salt solution (6% w/v, $KH_2PO_4$), 3 ml; (c) myo-inositol, 100 mg/l; (d) Vitamix (Marton and Browse, *Plant Cell Reports*, 10: 235-239 (1991), 2 ml.; (e) sucrose, 30 g/l; (f) supplemented with the plant growth regulators: (i) adenine hemisulfate, 80 mg/l; (ii) picloram, 0.12 mg/l; (iii) indole-3-butyric acid, 1.0 mg/l; (iv) 2,4-dichlorophenoxyacetic acid, 0.5 mg/l; (v) dimethylallyladenine, 0.5 mg/l; (vi) zeatin, 0.5 mg/l; and (vii) thidiazuron, 3 mg/l.

In some embodiments, the medium is solidified with a gellant. Gellants of the present invention include, but are not limited to, gellan gum, PHYTAGEL™, GELCARIN®, GELRITE®, food grade gellan gum, agarose, and the like. The gellant used to solidify the primary medium can be used at conventional concentrations. In one embodiment, the medium is solidified with PHYTAGEL™, 2 g/l.

In an additional embodiment of the present invention, the auxin in the primary medium is 2,4-dichlorophenoxyacetic acid, which is present in a concentration of about 0.2 mg/l, and the cytokinin in the primary medium is thidiazuron, which is present in a concentration of about 0.02 mg/l.

In further embodiments of the present invention, the pH of the medium for the primary cultivation step is adjusted to 5.6-5.8 before the medium is sterilized. In a further embodiment, the pH of the medium for the primary cultivation step is adjusted to 5.8 before the medium is sterilized. In one embodiment, the medium is sterilized in an autoclave or pressure cooker for 25-35 minutes at a temperature of about 105° C. to about 121° C. In another embodiment, the temperature at which the medium is sterilized is about 109° C.

The warm medium may be poured into a sterile culture dish and allowed to cool to room temperature. The chopped explant material can be distributed upon the surface of the gelled medium, and the culture dish covered with a lid and sealed to preserve sterility. The culture dish can be sealed with a strip of film such as food service film, parafilm, pallet wrap, and the like. The covered, sealed dish can then be placed in a location suitable for maintaining the temperature, as discussed above.

In yet further embodiments of the present invention, the tissue being cultured is kept in the dark during the primary cultivation step. In other embodiments, the tissue can be maintained in the light during the primary cultivation step. Exposure to light includes, but is not limited to, continuous illumination and intermittent illumination. Illumination can include natural light (e.g., greenhouse), or artificial light. The artificial light can be a mixture of incandescent light and cool white fluorescent tubes. If continuous artificial illumination is employed, the intensity can be in a range from about 30 µmol $m^{-2}s^{-1}$ to about 200 µmol $m^{-2} s^{-1}$, or more.

Figure 3:
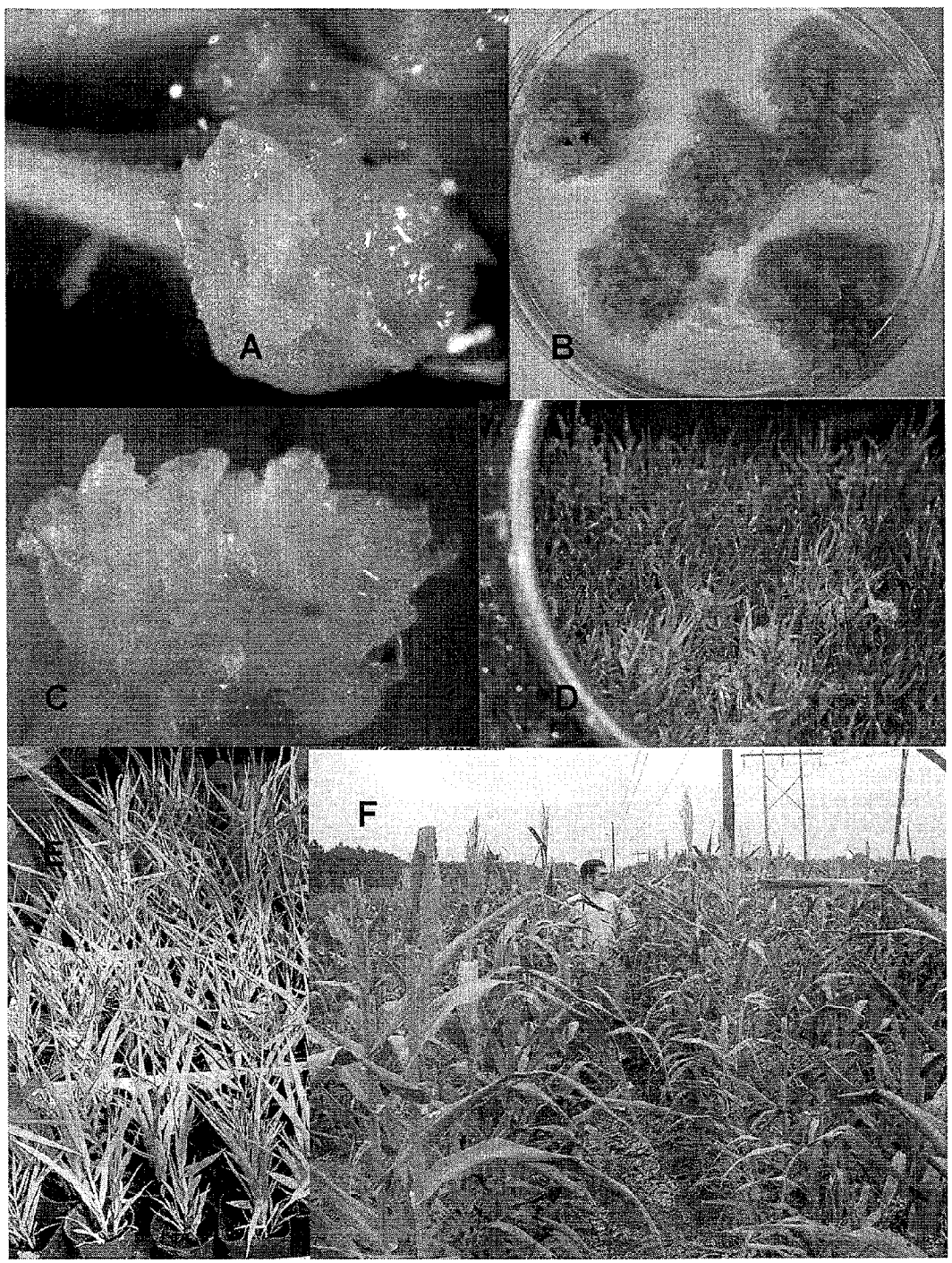
FIG. 3 shows the stages of in vitro culture, multiplication, and regeneration of *Arundo donax* via sustained totipotent embryogenic cell culture.

During the primary cultivation step totipotent embryogenic cell culture forms from the cut-up explant tissue, which can be further subcultured and maintained on the primary or secondary culture medium. Certain sectors of the cell culture can give rise to unipolar embryos which form multiple apical shoot meristems without significant shoot elongation. The culture at this point comprises both totipotent cell culture and tissue culture sectors (also referred to herein as totipotent or regenerable tissue culture). The totipotent tissue culture sectors can be transferred to fresh primary cultivation medium for sustained maintenance or they may be transferred to secondary cultivation medium for sustained propagation. Alternatively, totipotent tissue culture sectors can be transferred to tertiary medium under light to induce greening and rooting and further propagation or they can be transferred to hormone-free quaternary medium under light for the development of root systems and fully elongated shoots. Therefore, the totipotent tissue can be used as a regenerable source of genetic material for sustained maintenance and propagation. FIG. 3A shows *Arundo donax* in the primary cultivation step.

Micropropagation, Scaling Up and Storage.

Figure 4:
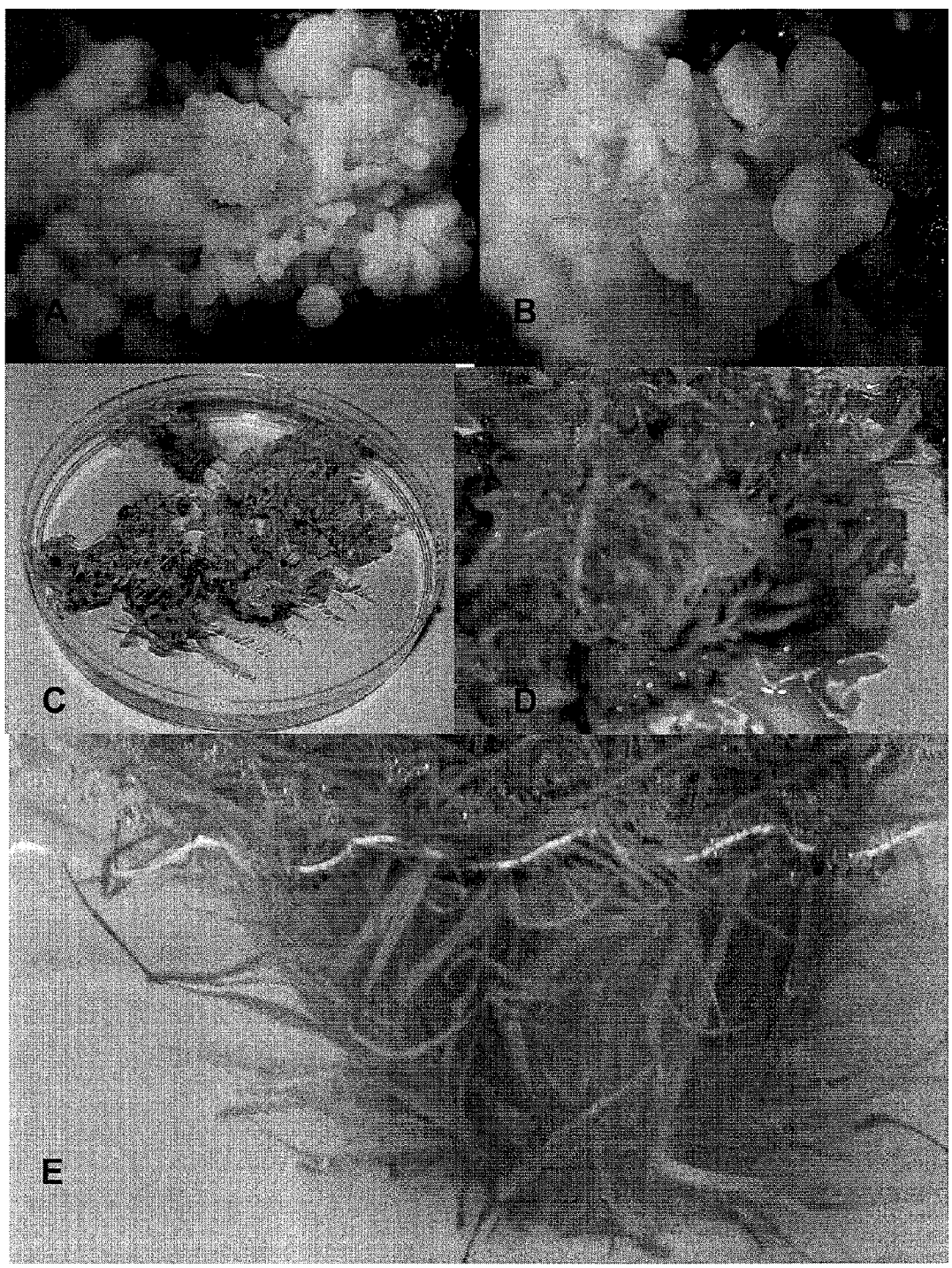
FIG. 4 shows the stages of in vitro culture, multiplication, and regeneration of *Miscanthus* x *giganteus* via sustained totipotent embryogenic cell culture.
Figure 5:
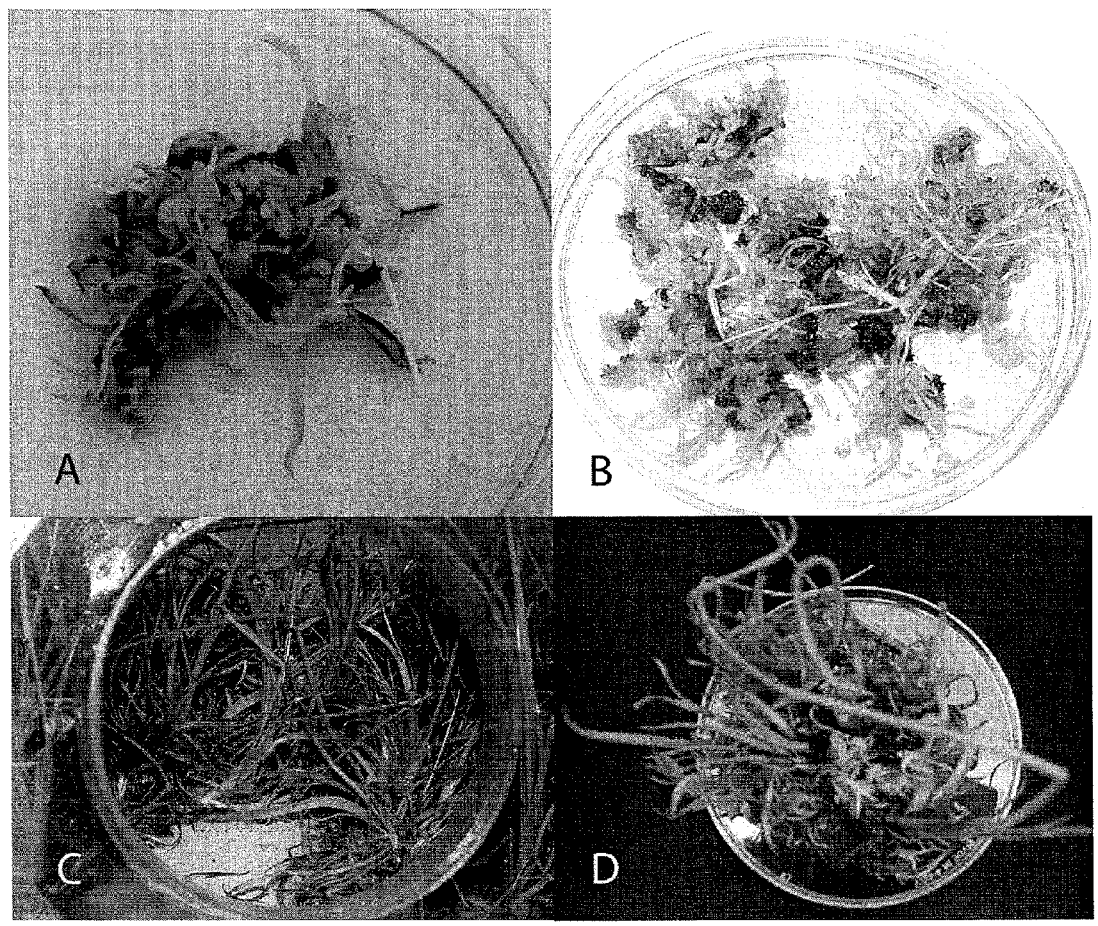
FIG. 5 provides examples of different monocot species produced using the methods described herein.

The totipotent embryogenic cell culture obtained in the primary cultivation step of the present invention can be maintained indefinitely on the primary cultivation medium with regular passage to fresh medium. In other embodiments, the totipotent embryogenic cell culture obtained in the primary cultivation step is transferred to a secondary cultivation medium in order to obtain a more friable embryogenic cell culture, which can also be maintained indefinitely on the secondary medium with regular passage to fresh medium. FIG. 3B shows a totipotent embryogenic cell culture of *A. donax* on secondary cultivation medium. FIG. 3C shows the formation of unipolar nonzygotic embryos of *A. donax* on secondary cultivation medium. Sustained totipotent embryogenic cell cultures of *Miscanthus* x *giganteus* on secondary culture media are shown in FIGS. 4A and 4B. FIG. 5 provides further examples of different monocot species produced using the methods described herein (*Miscanthus floridulus* (FIG. 5A); *Thysanolaena maxima* (FIG. 5B); *Scirpus validus* (FIG. 5C); *Scirpus californicus* (FIG. 5D)).

In some embodiments, the totipotent embryogenic cell cultures are maintained on the primary cultivation media or on secondary cultivation medium in the dark. In other embodiments, the totipotent embryogenic cell cultures are maintained on the primary cultivation media or on secondary cultivation medium in the light. When the cultures are grown in the presence of light, the light may be continuous or intermittent. Illumination can further include natural light (e.g., greenhouse) or artificial light. The artificial light can be a mixture of incandescent light and cool white fluorescent tubes. The intensity of the light used for culturing the tissue on secondary media can be in a range from about 30 µmol $m^{-2}s^{-1}$ to about 200 µmol $m^{-2}s^{-1}$ or more. Further, the intensity of light can be dim (less than 30 micromoles $m^{-2} s^{-1}$). One of ordinary skill in the art would recognize that even in the case of the dark grown cultures, exposure to light is possible when the cultures are subcultured or otherwise handled.

Accordingly, the present invention provides a method wherein after completion of the primary cultivation step, the totipotent tissue is cultivated in a secondary cultivation step during which multiplication continues. A medium that is useful for the secondary cultivation step (i.e., the secondary medium) can be any basal medium used for plant tissue culture. Such media are well known to those of skill in the art. In one embodiment, the secondary medium is supplemented with at least one plant hormone (e.g., plant growth regulator). Examples of suitable plant hormones include auxins and cytokinins.

Auxins of the present invention include not only auxin but also any compound with auxin-like activity. Thus, auxins used with the secondary media include, but are not limited to, 2,4-dichlorophenoxyacetic acid, picloram and indolebutyric acid and combinations thereof. Cytokinins of the present invention include not only cytokinin but also any compound with cytokinin-like activity. Thus, cytokinins to be used with the secondary media include, but are not limited to, thidiazuron, zeatin, benzyladenine, kinetin, adenine hemisulfate and dimethylallyladenine and combinations thereof. In some embodiments, the secondary medium is supplemented with at least one auxin and at least one cytokinin.

The secondary medium also comprises a carbon source, which can be any appropriate carbon source for tissue culture. Such carbon sources are known to those of ordinary skill in the art (Slater et al. *Plant Biotechnology, the Genetic Manipulation of Plants*, Oxford University Press, 368 pp., (2003)) and include, but are not limited to, sugars such as sucrose, glucose, maltose, galactose and sorbitol, and the like. In some embodiments of the present invention, the carbon source is sucrose.

In one embodiment of the present invention, the secondary medium is prepared by adding to sterile water: (a) MS (Murashige and Skoog, 1975) basal salts (Sigma Fine Chemicals, St. Louis, Mo.), 4.3 g/l; (b) Miller's salt solution (6% w/v, $KH_2 PO_4$ ), 3 ml; (c) myo-inositol, 100 mg/l; (d) Vitamix (Marton and Browse, *Plant Cell Reports*, 10: 235-239 (1991), 2 ml.; (e) sucrose, 30 g/l; (f) supplemented with the plant growth regulators: (i) adenine hemisulfate, 400 µM; (ii) 2,4-dichlorophenoxyacetic acid, 0.2 mg/l; (iii) thidiazuron, 0.01 µM. In some embodiments, the medium is solidified with a gellant. Gellants of the present invention are described above. In one embodiment, the secondary medium is solidified with PHYTAGEL™, 2 g/l.

In some embodiments of the present invention, the pH of the medium for the secondary cultivation step is adjusted to 5.6-5.8 before the medium is sterilized. In a further embodiment, the pH of the medium for the secondary cultivation step is adjusted to 5.8 before the medium is sterilized. The medium is sterilized in an autoclave or pressure cooker for 25-35 minutes at a temperature of about 105° C. to about 121° C. In some embodiments, the temperature at which the medium is sterilized is about 109° C.

The temperature for the secondary cultivation step is not critical and can be any temperature suitable for sustaining the proliferation of the totipotent cell culture. In representative embodiments, the temperature for the secondary cultivation step is in a range from about 15° C. to about 35° C. Thus, the temperature for the secondary cultivation step is about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., or any combination thereof. In some embodiments, the temperature range for the secondary cultivation step is about 15° C. to about 20° C., about 15° C. to about 25° C., about 15° C. to about 30° C., about 20° C. to about 25° C., about 20° C. to about 30° C., about 20° C. to about 35° C. or about 25° C. to about 30° C., and the like. In a further embodiment, the temperature range for the secondary cultivation step is about 26° C. to about 28° C. In a still further embodiment, the temperature range for the secondary cultivation step is about 25° C. FIGS. 1A-C and FIGS. 3B-C show *Arundo donax* in the secondary cultivation stage. *Miscanthus* x *giganteus* in the secondary cultivation stage is pictured in FIGS. 4a and 4B, while *Miscanthus floridulus* in the secondary cultivation stage is shown in FIG. 5A. FIG. 5B illustrates *Thysanolaena maxima* in the secondary cultivation stage.

The totipotent cell culture can be maintained and propagated indefinitely on secondary medium. Similar to the totipotent cell culture maintained on primary medium, the multiplication rate of the totipotent cell culture maintained on secondary medium is increased by treatment with a cold temperature. Thus, in particular embodiments, methods for cold treatment of the totipotent cell culture on secondary medium are the same as provided above for the totipotent cell culture on primary medium. According to particular embodiments of the present invention, the secondary medium is preferred for the maintenance and the cold treatment of the totipotent cell culture.

In further embodiments of the present invention, the cold treatments are incorporated into the micropropagation cycle. Accordingly, in one embodiment, a micropropagation cycle for the embryogenic cell culture is provided wherein the micropropagation cycle (subculture intervals) is 2-6 weeks in the dark at ambient temperature with intercalation of a cold treatment in the dark at 4-10° C. In representative embodiments, the cold treatment comprises treating the embryogenic cell culture with a cold temperature for a period in a range of about one month to about ten months, or longer. Thus, the cold treatment can be about one, two, three, four, five, six, seven, eight, nine, ten, eleven or twelve months, and the like. In particular embodiments, the cold treatment can be about one week, two weeks three weeks, four weeks, five weeks, six weeks, seven weeks, or eight weeks, and the like. In further embodiments, the cold treatment can be about 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 145, 150, 160, 170, 180, 190, 200, 205, 210, 215, 220, 225, 230, 235, 240, 245, 250, 255, 260, 265, 270, 275, 280, 285, 290, 295, 300, 305, 310, 315, 320, 330, 335, 340, 345, 350, 355, 360, 365 days, or any combination thereof. In further embodiments, the cold treatment can be in a range from about 2 weeks to about 6 weeks, about 2 weeks to about 8 weeks, about 2 weeks to about 10 weeks, about 2 weeks to about 12 weeks, about 2 weeks to about 14 weeks, about 2 weeks to about 16 weeks, about 4 weeks to about 8 weeks, about 4 weeks to about 12 weeks, about 4 weeks to about 16 weeks, about 4 weeks to about 20 weeks, about 4 weeks to about 24 weeks, about two months to about four months, about two months to about six months, about two months to about eight months, about two months to about ten months, about two months to about twelve months, about four months to about six months, about four months to about eight months, about four months to about ten months, about four months to about twelve months, about six months to about eight months, about six months to about ten months, about six months to about twelve months, or about six months to about fourteen months, and the like. In a particular embodiment, the cold treatment is in a range from about 4 weeks to about 6 weeks. The micropropagation cycle is useful with any of the media on which the totipotent cell culture is maintained and propagated.

The present invention further provides a method of prolonged or long-term cold treatment (i.e., cold storage) of the embryogenic cell cultures established on the secondary medium. Thus, the present invention further provides a method wherein the totipotent embryogenic cell culture can be stored long-term at a cold temperature. Accordingly, cultures produced in excess of the minimum mass required for maintenance can be maintained and stored at a cold temperature in order to build up stock. In some embodiments, the cold storage occurs in the dark. In other embodiments, the cell cultures are stored at a cold temperature in the light. In particular embodiments, the cultures can be maintained on spent medium. As previously described, the inventors have found that the cultures maintained in the dark while in cold storage exhibit increased rates of multiplication rates and increased longevity over those maintained in the light. The duration and temperature of the long-term or prolonged cold storage is the same as that described above for the cold treatments of the totipotent embryogenic cell cultures.

In additional embodiments, the totipotent embryogenic cell culture, which is being stored long-term at a cold temperature, is subcultured during the storage. In other embodiments, the totipotent embryogenic cell culture, which is being stored long-term at a cold temperature is not subcultured during the storage. Cultures that are maintained in storage for a prolonged time or long-term need to be "rehabilitated." Rehabilitation refers to transferring of the stored cultures to fresh media. In some embodiments, when the cultures are brought out of storage, the subculturing or transfer to fresh media occurs every two to six weeks. In other embodiments, the subculturing can occur about every four to six weeks, about every one to eight weeks or about every two to eight weeks, and the like. In further embodiments, the subculturing occurs about every week, about every two weeks, about every three weeks, about every four weeks, about every five weeks, about every six weeks, about every eight weeks, and the like. Once the cultures are brought out of storage, the subculturing is generally done on a regular basis.

Micropropagation as Multishoot Cultures.

After completion of the secondary cultivation step on the secondary medium, the totipotent tissue can then be transferred to a tertiary medium in which multiplication continues and complete plantlets are induced. Thus, according to embodiments of the present invention a method is provided wherein the totipotent embryonic cell culture is transferred from the secondary medium to a tertiary medium in order to continue multiplication of the cell culture and to produce a plantlet with roots and shoots. FIG. 3D shows plants of *A. donax* regenerated from the embryogenic cell culture and multiplying in tertiary culture medium. Examples of *Miscanthus* x *giganteus* plants regenerated from the embryogenic cell culture on tertiary medium are provided in FIGS. 4C, 4D and 4E. FIG. 5D shows *Scirpus californicus* plants regenerated from the embryogenic cell culture on tertiary medium.

A medium that is useful for the tertiary cultivation step (i.e., tertiary medium) can be any basal medium used for plant tissue culture. Such media are well known to those of skill in the art. In one embodiment, the tertiary medium is supplemented with at least one plant hormone (e.g., plant growth regulator). Examples of plant hormones suitable for the tertiary medium include cytokinins and compounds with cytokinin-like activity. Thus, in some embodiments, the only hormone present in the tertiary medium is cytokinin. Cytokinins useful in the present invention include, but are not limited to, thidiazuron, zeatin, benzyladenine, kinetin, adenine hemisulfate and dimethylallyladenine, and combinations thereof. In one embodiment, the tertiary medium is supplemented with thidiazuron. The present invention additionally provides a method wherein the plant hormone is supplemented in the tertiary medium at a concentration that is lower than that used in the primary medium.

The inventors note that the use of the synthetic cytokinin, thidiazuron, in the present invention resulted in a surprising effect. As previously discussed, embryogenic callus is typically obtained from monocots by inducing the primary cell culture on a medium containing one or more auxin or auxin-type plant hormones followed by a secondary cultivation step on a lowered auxin concentration but in the presence of a cytokinin or cytokinin-type plant hormone. The embryogenic potential of monocot cell cultures produced by these methods diminishes over time and making it necessary to repeatedly reinitiate the primary cell culture (U.S. Pat. No. 6,153,812 issued Nov. 28, 2000; Trigiano and Gray, *Plant tissue culture concepts and laboratory exercises*. Second ed., Boca Raton: CRC Press (2000)). In contrast, the hormone combination taught in the present invention has an unexpected result in that the primary callus induced from the explant already shows embryogenesis without the need for a secondary cultivation step and that the embryogenic capacity does not diminish over time.

As known to those of skill in the art, cytokinins, both natural and synthetic, are used to induce shoot formation while inhibiting root formation (Trigiano and Gray, *Plant tissue culture concepts and laboratory exercises*. Second ed., Boca Raton: CRC Press (2000)). However, in the present invention, the use of cytokinin, such as the synthetic cytokinin thidiazuron, produced a surprising effect in that upon transfer from the primary cultivation medium containing a combination of auxins and cytokinins to a medium without auxin but maintaining the cytokinin (e.g., thidiazuron) not only was shoot elongation promoted but unexpectedly root formation also resulted.

In some embodiments, the medium for tertiary cultivation (i.e., the tertiary medium) as provided by the present invention comprises a carbon source. The carbon source for the tertiary medium can be any appropriate carbon source known to those of ordinary skill in the art (Slater et al. *Plant Biotechnology, the Genetic Manipulation of Plants*, Oxford University Press, 368 pp., (2003)). Carbon sources useful for the tertiary medium include, but are not limited to, sugars such as sucrose, glucose, maltose, galactose and sorbitol, and the like. Similarly to the primary and secondary media, the preferred carbon source for the tertiary medium is sucrose.

In one embodiment, the tertiary medium is prepared by adding to sterile water (a) the cytokinin, thidiazuron; (b) sucrose, 30 g/l; (c) Miller's salt solution (6% w/v, $KH_2PO_4$), about 3 ml; and (d) MS salts, 4.3 g/l. In one embodiment the concentration of the thidiazuron is from about 0.01 mg/l to about 1 mg/l. In another embodiment, the concentration of the thidiazuron is about 0.02 mg/l.

The tertiary medium can be gelled and sterilized as described for the primary and secondary medium. Totipotent tissue from the secondary cultivation step can then be used to inoculate the tertiary medium. The inoculated tertiary cultivation medium is then cultured, under any light regime in order to obtain rooted plants. The tertiary cultivation step can be carried out for any period of time or at any temperature sufficient to obtain elongation of shoots and rooted plants. In one embodiment, the culture conditions include continuous light, about room temperature, for a period of from about one week to about four weeks.

In further embodiments, the tertiary medium comprises the cytokinin thidiazuron. In still further embodiments, the thidiazuron is present in the tertiary medium in a concentration of about 0.02 mg/l.

The temperature and the duration of the tertiary cultivation step is not critical and can be any temperature or duration sufficient for the production of complete plantlets with roots and partially elongated shoots. In representative embodiments, the temperature and duration for the tertiary cultivation step is similar to that described above for the primary cultivation step.

In the case of the monocot plants of the present invention (for example, *Arundo donax, Thysanolaena maxima, Miscanthus x giganteus, Miscanthus floridulus, Scirpus validus* and *Scirpus californicus*), the tertiary cultivation step results in complete plantlets with roots and partially elongated shoots that conveniently fit the commonly used plant propagation containers. Further, the resulting tertiary cultures do not interfere with handling of the plantlets with the tools used for transfer during division of the cultures.

The embryogenic cell culture obtained in the primary cultivation step can be maintained indefinitely on the tertiary cultivation medium with regular passage to fresh media. The method is therefore suitable not only for sustained maintenance and propagation of the totipotent cell culture lines but for maintenance of sustained regenerating tissue culture lines as well.

Acclimatization and Planting.

Upon completion of the tertiary cultivation step, the plantlets can be moved either directly to soil for acclimatization, or they can be transferred to a quaternary medium to permit gradual acclimatization to non-sterile and photoautotrophic conditions. Acclimatization generally involves an introduction of a plantlet to ambient air conditions including moisture, temperature and non-sterility. In one embodiment, acclimatization comprises gradually removing the lids of the culture dishes to expose the plantlets on quaternary media to lower humidity and non-sterile conditions. Acclimatization typically further comprises stimulating the plantlet to begin photosynthesizing by the fact that the quaternary media and/or the soil do not provide a freely available carbon source such as sucrose.

In one embodiment, the plantlets are transferred from the tertiary medium to a quaternary medium that is similar to the medium used for the tertiary cultivation step, but which is free of plant hormones, vitamins and a carbon source.

The quaternary cultivation step can be carried out for any period of time and at any temperature sufficient to acclimatize the plantlets. Thus, in representative embodiments, the temperature for the quaternary cultivation step is similar to that described for the primary and secondary cultivation steps. In particular embodiments, the quaternary cultivation step can be carried out at substantially room temperature.

In an exemplary embodiment, the duration of the quaternary step can be in the range from about one week to about four weeks or more. In further embodiments, the duration of the quaternary step can be one, two, three, and four weeks, and the like. In additional embodiments, the duration can be one month, two months, three months or more. In still further embodiments, the duration for the quaternary step is from about one week to about three weeks, about one week to about five weeks, about one week to about six weeks, about one week to about eight weeks, about two weeks to about four weeks, about two weeks to about six weeks, about two weeks to about eight weeks, about two weeks to about twelve weeks, or about four weeks to about eight weeks, and the like.

A medium that is useful for the quaternary cultivation step (i.e., the quaternary medium) can be any basal medium used for plant tissue culture. Such media are well-known to those of skill in the art and include, but are not limited to, MS medium, and Gamborg's B5 medium (full or ½ strength) without a carbon source, vitamins, hormones or any other additive, such as nutrient mixtures, buffers, antifungal compounds, amino acids, organic acids, nucleotides, nucleosides, bases, hardening agents and the like.

An example of *A. donax* plants transferred to pots from quaternary medium following acclimatization is provided in FIG. 3E. FIG. 5C shows *Scirpus validus* in the acclimatization stage.

Transportation.

Biotechnological field applications such as habitat restoration, remediation and biomass production require the production of propagules at an industrial scale. Depending on the scale, part or all of the propagation technology needs to be deployed to a location convenient to the vicinity of the application. Thus, storage and mobilization of stockpiles of propagules in the appropriate developmental stage are necessary for these applications.

For industrial-scale planting, the present invention provides methods wherein the cultures, plantlets or plants from any of the various cultivation steps described herein can be moved near the location of final planting. In some embodiments of the present invention, after completing the secondary cultivation step, the culture dishes that are filled with the totipotent tissue are accumulated in cold-storage in a sufficient number for a particular planting project. The dishes can be transported by any means of transportation in a cold compartment to a suitable propagation facility where they can then be unpacked and propagated further as needed or transferred to tertiary medium.

The compartment in which the cultures, plantlets and plants are transported can be insulated or refrigerated. When the transportation time is less than 3 weeks, the compartment used to transport the cultures, plantlets or plants may be insulated and maintained at ambient temperatures. When the time needed for transportation is three weeks or more, or conditions otherwise require it, the cultures, plantlets or plants may be transported in compartments maintained at a cold temperature. The temperatures of the cold compartment can be about the same as those described above for the cold treatment and cold storage of embryogenic cell cultures.

The plant materials of the present invention that can be transported include any of the plant materials described herein including the embryogenic cell culture, tissue culture, plantlets, plants or propagules. Thus, in one embodiment of the present invention, propagules are transported as embryogenic cell cultures in culture dishes on semisolid medium in the dark at ambient temperatures or at cold storage temperatures. The types of propagules that can be transported include, but are not limited to, tertiary microtillering shoot cultures in liquid, tertiary microtillering shoot cultures on semisolid culture medium in vessels or bags, microtillering multishoot cultures in sugar-free liquid cultures in vessels, and acclimatized bare-root plants packaged. The choice of propagule transported depends on the need, demand and conditions at the location.

The distances over which the plant materials can be transported can be long or short distances. Thus, the plant materials can be maintained in transit for about one day or less or for about 30 days or more.

Thus, as described herein, the cold treatments of the present invention serve multiple purposes. Cold treatments can improve the longevity of the tissue culture, plantlets, plants and propagules, allow safe and cost effective transportation and/or accelerate totipotent growth once the plant materials are unpackaged and further cultured at the final destination site. FIG. 3F shows a stand of *A. donax* plants established from in vitro cloned plants.

Enhanced Somaclonal Breeding and Genetic Manipulation.

A major limiting factor associated with emerging biotechnological applications of nontraditional crop plants is the lack of elite plant material. Elite plant material is plant material selected for desirable genotypic and phenotypic characteristics. As such, elite plant material includes, but is not limited to, vegetative clones, F1-hybrids, and inbred plant materials selected for desirable genotypic and phenotypic characteristics. Classical breeding technology predominantly relies on the use of inbred (pure) lines, crosses, and analysis of progenies. Pure lines are rarely available for environmentally important wild plant species and obtaining them is very tedious process. The use of totipotent tissue cultures of the present invention to induce somaclonal (genetic and/or epigenetic) variation in clonal plant materials can provide shortcuts and improved efficiency.

Accordingly, one embodiment of the present invention provides a method of producing an elite plant line comprising: selecting for at least one trait of interest in the totipotent embryogenic cell culture and/or plantlet produced by the methods of the present invention, wherein the at least one trait of interest is a result of somaclonal variation or the introduction of at least one heterologous nucleotide sequence genome of a cell of the totipotent embryogenic cell culture and/or plantlet, and cultivating the totipotent embryogenic cell culture and/or plantlet comprising the at least one trait of interest to produce an elite plant line.

The present invention provides further embodiments, wherein the at least one trait of interest is resistance and/or increased tolerance to an environmental condition. In some embodiments, the increased tolerance is to the presence of a chemical pollutant in the environment. In other embodiments, the resistance or increased tolerance is to a halogenated phenol or other xenobiotic. In additional embodiments, the resistance or increased tolerance is to salts.

In still further embodiments, other characteristics for which elite lines may be selected for include, but are not limited to, improved morphology, improved biomass parameters, improved pest and pathogen tolerance, and any combination thereof. The improved biomass parameters include, but not limited to, cellulose/lignin ratio and fiber quality, and any combination thereof.

By increasing the length and volume of the totipotent phase, especially the embryogenic cell culture phase, somaclonal variations will be increased; thus, allowing for a very efficient cellular level selection of elite lines originated from somaclonal or gene transfer events. In some embodiments, the totipotent sustained secondary cultures of the present invention further increase the efficiency of selection by extending the selection for traits, which are expressed only at the level of differentiated shoots. Furthermore, in some embodiments, an altered elite population can be obtained without generation and characterization of individual lines, if the selection pressure is constantly applied to the embryogenic cultures until the plants from the secondary cultures differentiate. The resultant altered elite population can be used directly in applications without further reducing the natural genetic variation in the elite population by a second cloning event.

The sustained totipotent cell cultures also provide an excellent system for all forms of molecular breeding including the introduction of genes of interest and complex genetic constructs, using genetic transformation for genetic and epigenetic manipulation of these plants.

Thus, the present invention provides embodiments wherein the explant is selected from a transgenic plant stably transformed with at least one heterologous nucleotide sequence. In other embodiments, at least one heterologous nucleotide sequence is introduced into a cell of the totipotent embryogenic cell culture grown on either the primary or secondary medium to produce a stable transgenic totipotent embryogenic cell culture. Further embodiments comprise producing a transgenic plantlet and/or plant from the transgenic totipotent embryogenic cell culture.

Additional embodiments of the present invention comprise introducing at least one heterologous nucleotide sequence of interest into a cell of the embryogenic cell culture grown on tertiary medium to produce a stable transgenic embryogenic cell culture and/or a stable transgenic plantlet with shoots and roots. A further embodiment provides a method of introducing at least one heterologous nucleotide sequence of interest into a cell of a plantlet produced by the methods of the present invention grown on tertiary medium or quaternary medium to produce a stable transgenic plantlet with shoots and roots and/or a stable transgenic plant. In a still further embodiment, a method is provided wherein at least one heterologous nucleotide sequence is introduced into a cell of the acclimatized plantlet or plant produced by the methods of the present invention in order to produce a stable transgenic plantlet and/or plant.

The heterologous nucleotide sequence of interest can be any heterologous nucleotide sequence and includes, but is not limited to, nucleotide sequences that encode antibiotic resistance genes, pesticide resistance genes, salt resistance genes, mercuric reductase genes, organomercurial lyase gene, Bt-toxin genes, and any combination thereof. The nucleotide sequences of interest of the present invention can also encode siRNAs that down-regulate genes involved in lignin and polysaccharide biosynthesis. Lignin and polysaccharide biosynthesis genes are known to those of skill in the art (See, for example, Boerjan et al., *Annu. Rev. Plant Biol.* 54: 519-546 (2003) and Burton et al., *Planta* 221: 309-312 (2005)). Thus, genes involved in lignin biosynthesis include, but are not limited to, cinnamyl alcohol dehydrogenase, cinnamoyl coenzyme-A reductase, caffeic acid O-methyltransferase, caffeoyl-CoA O-methyl transferase, 4-coumarate-coenzyme A ligase, and the like. Genes involved in polysaccharide biosynthesis include, but are not limited to, glycosyltransferases, cellulose synthase complex, endoglucanases, and the like.

A nucleotide sequence can be introduced into a cell of an embryogenic cell culture or a plant cell by any method known to those of skill in the art. Procedures for transforming a wide variety of plant species are well known and routine in the art and are described throughout the literature. Such methods include, but are not limited to, transformation via bacterial-mediated DNA delivery, viral-mediated DNA delivery, silicon carbide or DNA whisker-mediated DNA delivery, liposome mediated DNA delivery, microinjection, microparticle bombardment, electroporation, sonication, infiltration, PEG-mediated DNA uptake, any other electrical, chemical, physical or biological mechanism that results in the introduction of DNA into the plant cell, and any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Bacterial mediated DNA delivery includes but is not limited to DNA delivery by *Agrobacterium* spp. and is described, for example, by Marton et al. (*Nature* 277:129-131 (1979)); Horsch et al. (*Science* 227:1229 (1985); Ishida et al. (*Nature Biotechnol.* 14:745 750 (1996)); and Fraley et al. (*Proc. Natl. Acad. Sci.* 80: 4803 (1983)). Transformation by various other bacterial species is described, for example, by Broothaerts et al. (*Nature* 433:629-633 (2005)).

Physical delivery of nucleotide sequences via microparticle bombardment is described, for example, in Sanford et al. (*Methods in Enzymology* 217:483-509 (1993)) and McCabe et al. (*Plant Cell Tiss. Org. Cult.* 33:227-236 (1993)).

Another method for physical delivery of DNA to plants is sonication of target cells. This method is described, for example, in Zhang et al. (*Bio/Technology* 9:996 (1991)). Alternatively, liposome or spheroplast fusion can be used to introduce nucleotide sequences into plants. Examples of the use of liposome or spheroplast fusion are provided in Deshayes et al. (*EMBO J.*, 4:2731 (1985), and Christou et al. (*Proc Natl. Acad. Sci. U.S.A.* 84:3962 (1987)). Direct uptake of DNA into protoplasts using $CaCl_2$ precipitation, polyvinyl alcohol or poly-L-ornithine is described, for example, in Hain et al. (*Mol. Gen. Genet.* 199:161 (1985)) and Draper et al. (*Plant Cell Physiol.* 23:451 (1982)). Electroporation of protoplasts and whole cells and tissues are described, for example, in Donn et al. (*In Abstracts of VIIth International Congress on Plant Cell and Tissue Culture IAPTC*, A2-38, p 53 (1990); D'Halluin et al. (*Plant Cell* 4:1495-1505 (1992)); Spencer et al. (*Plant Mol. Biol.* 24:51-61 (1994)) and Fromm et al. (*Proc. Natl. Acad. Sci.* 82: 5824 (1985)). Polyethylene glycol (PEG) precipitation is described, for example, in Paszkowski et al. (*EMBO J.* 3:2717 2722 (1984)). Microinjection of plant cell protoplasts or embryogenic callus is described, for example, in Crossway (*Mol. Gen. Genetics* 202:179-185 (1985)). Silicon carbide whisker methodology is described, for example, in Dunwell et al. (*Methods Mol. Biol.* 111:375-382 (1999)); Frame et al. (*Plant J.* 6:941-948 (1994)); and Kaeppler et al. (*Plant Cell Rep.* 9:415-418 (1990)).

In addition to these various methods of introducing nucleotide sequences into plant cells, expression vectors and in vitro culture methods for plant cell or tissue transformation and regeneration of plants are available for carrying out the methods of this invention. See, for example, Gruber et al., ("Vectors for Plant Transformation" in *Methods in Plant Molecular Biology and Biotechnology*, Glick, B. R. and Thompson, J. E., Eds. (CRC Press, Inc., Boca Raton, (1993), pages 89-119)

Accordingly, in one embodiment, a heterologous nucleotide sequence is introduced into a cell of the totipotent embryogenic cell culture or plant cell produced by the methods of the present invention by co-cultivation of the cell of the totipotent embryogenic cell culture with *Agrobacterium*

*tumefaciens* to produce a stable transgenic totipotent embryogenic cell culture or stable transgenic plant cell.

In a further embodiment, a method is provided, wherein a heterologous nucleotide sequence is introduced into a cell of the totipotent embryogenic cell culture or plant cell produced by the methods of the present invention by direct DNA transfer to produce a stable transgenic totipotent embryogenic cell culture or transgenic plant cell.

The methods of the present invention further provide producing a stable transgenic plantlet and/or plant from the transgenic totipotent embryogenic cell culture or transgenic plant cell. Methods of selecting for stably transformed transgenic cell culture, plant cells or plants are routine in the art.

Production of Purpose-oriented Plant-microbe Associations.

The sustained aseptic totipotent cell cultures and multi-shoot cultures of the present invention also provide an excellent system for the production of microbial-plant associations before acclimatization and transfer to soil. The microbial species or consortium is selected with a particular application in mind and can be tuned for providing fitness in a particular planting location or for contributing facultative metabolic functions that, in synergy with the plant's own metabolism, provide enhanced metabolic capabilities that are useful for various applications such as phytoremediation or raw material conversion.

Accordingly, the present invention provides a method of establishing a plant-microbe association comprising co-cultivating at least one plantlet and/or plant produced by the methods of the present invention with at least one microbial species in a quaternary medium to establish a plant-microbe association. As described previously, the quaternary medium of the present invention lacks plant hormones, a carbon source and vitamins. In one embodiment of the invention, one microbial species is co-cultivated with at least one plantlet and/or plant produced by the methods of the present invention to establish a plant-microbe association. In other embodiments, two or more microbial species are co-cultivated with at least one plantlet and/or plant produced by the methods of the present invention.

In representative embodiments, the at least one plant and/or plantlet is selected from plantlets growing on the tertiary medium. In other embodiments, the at least one plantlet and/or plant is a plantlet or plant growing on quaternary medium. In still other embodiments, the at least one plantlet or plant is a plant or plantlet that is growing on soil. Additionally, the at least one plantlet or plant can be from elite plant lines produced by the methods of the present invention.

Microbial species that can be used to establish a plant-microbe association include, but are not limited to, *Pseudomonas mallei, Pseudomonas fluorescens, Pseudomonas aeruginosa, Pseudomonas cepaica, Acinetobacter lwoffi, Acinetobacter baumanni, Bacillus licheniformis, Bacillus cereus* and *Phyllobacterium* spp., and combinations thereof. In further embodiments of the invention, a plantlet having an established plant-microbe association is acclimated to non-sterile and photosynthetic conditions.

Thus, in some embodiments of the invention the plant-microbial association is between *Arundo donax* and a microbe selected from the group consisting of *Pseudomonas mallei, Acinetobacter baumanni, Acinetobacter lwoffi, Pseudomonas cepaica, Pseudomonas aeruginosa, Pseudomonas fluorescens, Bacillus cereus, Bacillus licheniformis*, and *Phyllobacterium* spp., and combinations thereof.

In other embodiments, the plant-microbial association is between *Thysanolaena maxima* and a microbe selected from the group consisting of *Pseudomonas mallei, Acinetobacter baumanni, Acinetobacter lwoffi, Pseudomonas cepaica, Pseudomonas aeruginosa, Pseudomonas fluorescens, Bacillus cereus, Bacillus licheniformis*, and *Phyllobacterium* spp., and combinations thereof.

In further embodiments, the plant-microbial association is between *Miscanthus* x *giganteus* and a microbe selected from the group consisting of *Pseudomonas mallei, Acinetobacter baumanni, Acinetobacter lwoffi, Pseudomonas cepaica, Pseudomonas aeruginosa, Pseudomonas fluorescens, Bacillus cereus, Bacillus licheniformis*, and *Phyllobacterium* spp., and combinations thereof.

In yet further embodiments, the plant-microbial association is between *Miscanthus floridulus* and a microbe selected from the group consisting of *Pseudomonas mallei, Acinetobacter baumanni, Acinetobacter lwoffi, Pseudomonas cepaica, Pseudomonas aeruginosa, Pseudomonas fluorescens, Bacillus cereus, Bacillus licheniformis*, and *Phyllobacterium* spp., and combinations thereof.

In some embodiments of the present invention, the plant-microbial association is between *Scirpus californicus* and a microbe selected from the group consisting of *Pseudomonas mallei, Acinetobacter baumanni, Acinetobacter lwoffi, Thysanolaena maxima, Pseudomonas cepaica, Pseudomonas aeruginosa, Pseudomonas fluorescens, Bacillus cereus, Bacillus licheniformis*, and *Phyllobacterium* spp., and combinations thereof.

In other embodiments, the plant-microbial association is between *Scirpus validus* and a microbe selected from the group consisting of *Pseudomonas mallei, Acinetobacter baumanni, Acinetobacter lwoffi, Pseudomonas cepaica, Pseudomonas aeruginosa, Pseudomonas fluorescens, Bacillus cereus, Bacillus licheniformis*, and *Phyllobacterium* spp., and combinations thereof.

After completing the co-cultivation step, the dishes can be transported by any means of transportation to a suitable propagation facility where the plants can then be unpacked and acclimatized, and transplanted into soil.

Phytoremediation.

The present invention further provides methods directed to phytoremediation. Phytoremediation can be used to remove pollutants from the environment including, but not limited to, xenobiotic compounds and other compounds or pollutants such as those present in the environment in concentrations that are higher than normal.

Thus, in one embodiment, phytoremediation comprises establishing a plurality of plants produced by the methods of the present invention and possessing the same genetic characteristics in a liquid medium, and contacting the roots of the plants with an environmental pollutant in the liquid medium, thereby causing the environmental pollutant to be removed from the liquid medium.

In other embodiments, phytoremediation comprises establishing a plurality of plants produced by the methods of the present invention and possessing the same genetic characteristics in a land area and contacting the roots of the plants with an environmental pollutant in the land area, thereby causing the environmental pollutant to be removed from the land area.

In representative embodiments, a plurality of plants comprises at least two plants. For example, in some embodiments, a plurality of plants comprises 10 plants. In further exemplary embodiments, a plurality of plants comprises hundreds or thousands of plants.

The plants of the present invention that can be used in phytoremediation include but are not limited to those plants that are produced from wild plants, cultivated plants (greenhouse and field grown), and plants regenerated from explants produced by the methods of the present invention. In addition, plants of the present invention that can be used in phytoremediation comprise elite lines produced using the methods described herein.

The present invention is explained in greater detail in the following non-limiting Examples.

EXAMPLES

Example 1

Increased Multiplication Rate by Cold Treatment of *Arundo* embryogenic cell culture.

The multiplication rate of *Arundo* embryogenic cell culture on secondary culture medium is increased by a six-month pretreatment in the cold as well as by reducing the size of initial inoculum. An increase in the proportion of embryogenic cells is also apparent after cold treatment resulting in about a 50% increase in yield. In the case of large-scale propagation where subculturing is the rate limiting step (manual work under sterile hood conditions), the cold treatments result in a dramatic increase in efficiency. Table 1 shows the data for two levels of initial mass to medium ratios and further shows that a smaller initiation mass results in much higher multiplication rates.

TABLE 1

Initial mass to medium ratio of *Arundo* embryogenic cell culture on secondary culture medium.

| Without cold treatment | | | With cold treatment | | |
|---|---|---|---|---|---|
| Intial mass [g] | Final mass [g] | Fold Increase | Intial mass [g] | Final mass [g] | Fold Increase |
| 1.60 | 5.96 | 3.7 | 1.14 | 6.32 | 5.5 |
| 1.95 | 6.04 | 3.1 | 1.53 | 6.31 | 4.1 |
| 2.33 | 7.04 | 3.0 | 0.91 | 4.60 | 5.1 |
| 1.93 | 6.11 | 3.2 | 1.27 | 5.31 | 4.2 |
| 1.10 | 4.27 | 3.9 | 1.25 | 5.90 | 4.7 |
| 1.60 | 5.68 | 3.6 | 1.59 | 6.62 | 4.2 |
| 1.48 | 3.76 | 2.5 | 1.06 | 7.60 | 7.2 |
| 1.20 | 3.10 | 2.6 | 1.27 | 5.41 | 4.3 |
| 1.65 | | 3.2 ± 0.2 | 1.25 | | 4.9 ± 0.4 |
| 0.60 | 4.22 | 7.0 | 0.61 | 5.86 | 9.6 |
| 0.69 | 4.25 | 6.2 | 0.70 | 6.50 | 9.3 |
| 0.72 | 5.01 | 7.0 | 0.59 | 5.77 | 9.8 |
| 0.67 | 4.13 | 6.2 | 0.66 | 5.41 | 8.2 |
| 0.72 | 4.34 | 6.0 | 0.55 | 5.45 | 9.9 |
| 0.73 | 4.85 | 6.6 | 0.53 | 4.99 | 9.4 |
| 0.69 | | 6.5 ± 0.2 | 0.61 | | 9.4 ± 0.3 |

While not wishing to be bound by any particular theory of the invention, cold storage not only delays senescence but, as discussed above, induces lasting physiological changes that cause an increased embryogenic growth rate after recovery at normal growth temperature. The enhanced growth rate has been maintained at least for 2-3 months after treatment under prolonged cold conditions. Viability was retained at 100% in the cold (at 5-10° C.) for at least 10 months with testing every 4 weeks. Recovery from cold storage (and totipotency) can be monitored by transferring the cultures into differentiation inducing conditions (secondary medium under light and culture room conditions (25-27° C.)) and measuring the changes of chlorophyll content (a good indicator of the amount of shoot differentiation in this system) as well as the growth rate.

It is noted that the present inventors initiated the first embryogenic culture of *Arundo donax* in 1998 and this culture has been maintained without loss of regeneration ability for more than 8 years. The methods of the present invention have also allowed the initiation of embryogenic cell cultures consistently from this same wild clone of *Arundo* and from other ecotype clones from different habitats routinely every year. Several lines have been developed from the "Blossom", and "GT" ecotypes. To the best of the inventors' knowledge, the present invention is the first report of sustained totipotent embryogenic cell culture of *Arundo donax*.

The observed positive effects of cold treatment on the cultures were surprising, because *Arundo donax* as well as some of the other species of the present invention are Mediterranean or subtropical species and thus, are considered to be cold sensitive.

Example 2

Productivity and Propagation Yield

The following is an exemplary experiment showing the productivity and the propagation yield of the present invention.

1. Culture dish multiplication (primary and secondary cultures). A five to ten times multiplication rate per four weeks was achieved in the primary and secondary cultivation steps (0.6 g to 1 g→6 g to 7.5 g per 4 week cycle ). Approximately 200,000 to about 3,200,000 potential plants were transferred per hour (considering one to four tertiary subcultures). About 10 to 20 million potential plants were produced per m² embryogenic culture room floor space (considering a single tertiary subculture and 4000 dishes per m³ box).

2. Transfer to culture vessels (tertiary culture) and multiplication. About a four times multiplication rate per 3 week cycle (30 g→120 g) was achieved with about a 5% attrition rate. Thus, about 240,000 potential plants were transferred per hour.

The present invention resulted in a high volume output. Thus, from a single culture dish of embryogenic cell culture (6-7.5 g) after 12 weeks (four tertiary subcultures) 160,000 potential plants entered into the acclimatization process.

3. Quaternary culture: acclimatization (two to four weeks). Step 3 included plants ready for transfer to greenhouse flats as well as four week-old field ready plants.

Parameters used in the calculations include the following. Each fully-grown culture dish provides about 6 g to 7.5 g embryogenic culture, which is approximately 2,500 potential plants. The tertiary cultures are initiated using about 30 g of embryogenic tissue per vessel or four culture dishes of tissue per vessel. The fresh weight of a fully grown culture in one vessel is 120 g which is approximately 10,000 potential plants.

Example 3

Transformation of *Arundo donax* Explants Using *Agrobacterium tumefasciens*

Figure 6:
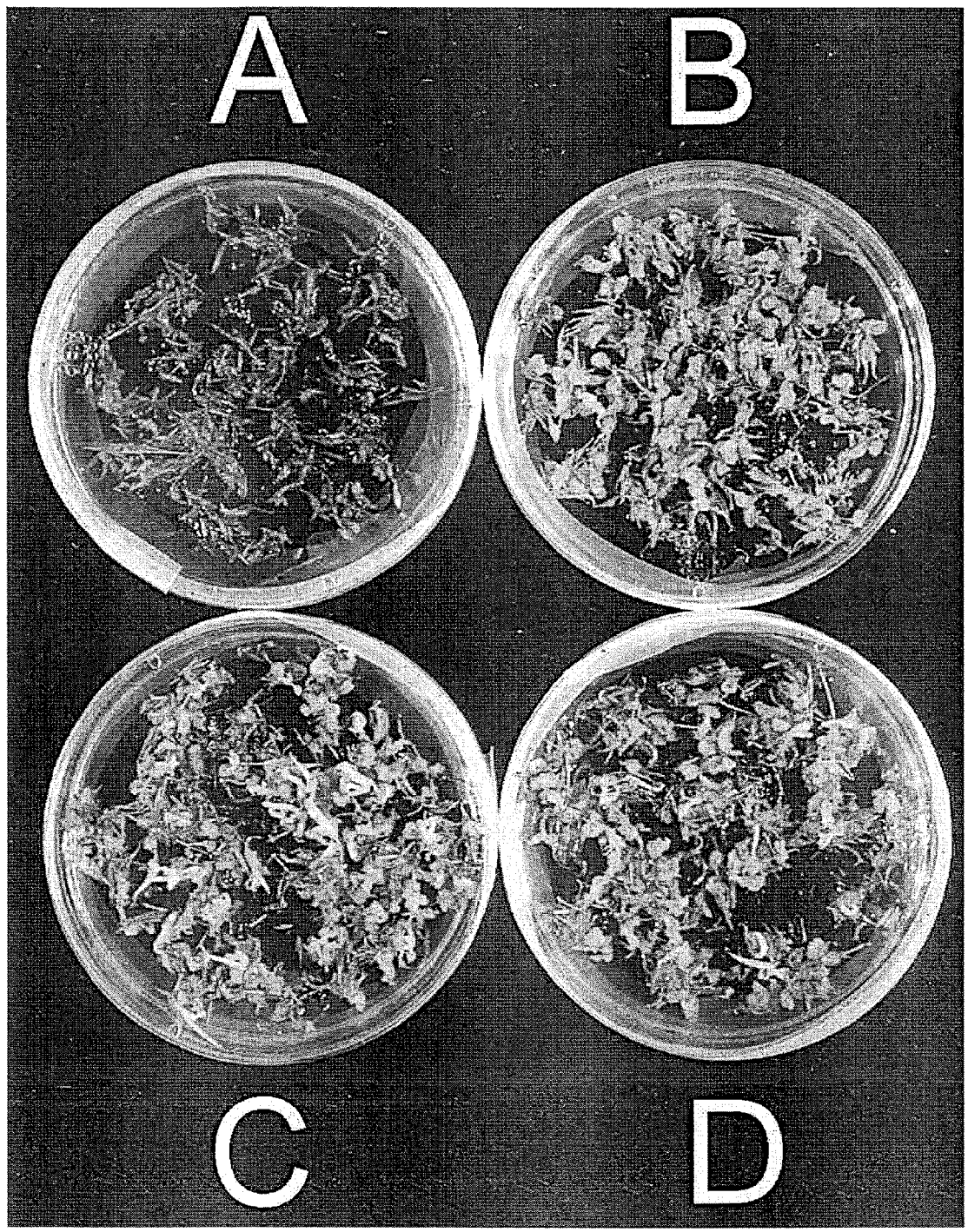
FIG. 6 shows selection of antibiotic resistant transformants four weeks after *Agrobacterium*-mediated gene transfer to cross-sectional segments of immature *Arundo donax* inflorescence (explants). Transformation is carried out by cocultivation of the embryogenic callus with *Agrobacterium tumefaciens* carrying plasmid pMSF3022.

*Agrobacterium tumefaciens* carrying the plasmid, pMSF3022, was used to transform *Arundo donax* explants (cross-sectional segments of immature inflorescence). Plasmid pMSF3022 carries the bar gene that confers resistance to phosphinothricin and provides a positive selection and the gfp (green fluorescent protein) gene which provides a visual selection of transformants. Antibiotic resistant transformants were selected for four weeks after gene transfer by incubating the explants on primary solid culture medium with or without phosphinothricin and containing ticarcillin at 400 m/L concentration to eliminate residual *Agrobacterium*. As shown in FIG. 6A control explants (untransformed) were killed by 10 mg/L of phosphinothricin (antibiotic/herbicide). In the absence of the antibiotic/herbicide, the control explants develop embryogenic callus (FIG. 6B). In contrast, the explants that were cocultivated with the *A. tumefaciens* carrying the plasmid, pMSF3022 (transformed), were able to develop embryogenic callus in the presence of 10 mg/L of phosphinothricin (FIG. 6C). FIG. 6D shows that cocultivated explants develop embryogenic callus in the absence of the antibiotic/herbicide.

Example 4

Somaclonal Variation in the Sustained Totipotent Embryogenic Cell Cultures

*Arundo donax* plants regenerated from the embryogenic cell cultures grown in liquid secondary growth medium as described herein show higher frequency of somaclonal variation than vegetative clones produced by cutting in the greenhouse. The trait chosen to demonstrate somaclonal variation is oxidative dehalogenation activity of cell-free extract of roots. The mean dehalogenation activity of the population was shown to increase in the embryogenic cell cultures grown in liquid secondary growth medium as compared to vegetative clones produced by cutting in the greenhouse.

1. Assay for oxidative dehalogenation activity. The calorimetric assay to measure oxidative dehalogenation measures peroxide-dependent enzymatic dehalogenation of 2,4,6-trichlorophenol (TCP) by cell-free extract of roots. TCP is an anthropogenic environmental pollutant, which is toxic to cell cultures and plants. Oxidative dehalogenation activity is proportional to total root peroxidase activity assayed by TCP, which conveniently acts as the chromogen in the reaction.

Roots are separated, rinsed with distilled water, blotted dry, and, if not used immediately, frozen in liquid nitrogen for temporary storage. Samples are weighed, frozen in dry ice-ethanol bath and homogenized in the extraction buffer (50 mM $KPO_4$ buffer, pH 5.3) in a microcentrifuge tube with a micro pestle. The homogenate is centrifuged at 15,000×g for 20 min.

For a standard enzyme assay, 500 µliter of the supernatant (crude extract) is added to 500 µliters of assay buffer. The assay buffer contains 20 mM $H_2O_2$, and 1 mM TCP in 20 mM Bistris buffer (pH 5.9, 25° C., 1 hr). The intensity of the color at 525 nm is proportional to the loss of TCP as measured by HPLC.

TCP removal from the liquid phase is assayed by measuring TCP on a 3.8×150 mm NovaPak-C18 reverse phase column (Part No. WAT086344, Waters 2690 HPLC separations module with Waters 996 photodiode array detector, Millenium32 Operating System, Waters Co.) under isocratic conditions (sample size, 50 µliters; flow rate, 1 ml/min, mobile system, acidic methanol (MeOH—5% acetic acid in water, 70:30 detection is at 289 nm)).

2. Preselection of the embryogenic cell cultures on a halogenated xenobiotic results in increased somaclonal variation. In order to preselect the embryogenic cell cultures, TCP is dissolved in methanol, filter sterilized and added to the autoclaved cooled medium just before solidification under aseptic conditions. Browning of the tissue occurs after three days on TCP concentrations of 0.3 mM or greater. The minimum concentration at which necrosis and growth arrest occurs is 0.24 mM. Partial browning occurs between 0.24 and 0.28 mM TCP, but some tissue survives even at this concentration. Preselection is carried out by growing embryogenic cell cultures on 0.24 mM TCP. Enzyme activity is assayed 2 months later (see above).

Figure 7:
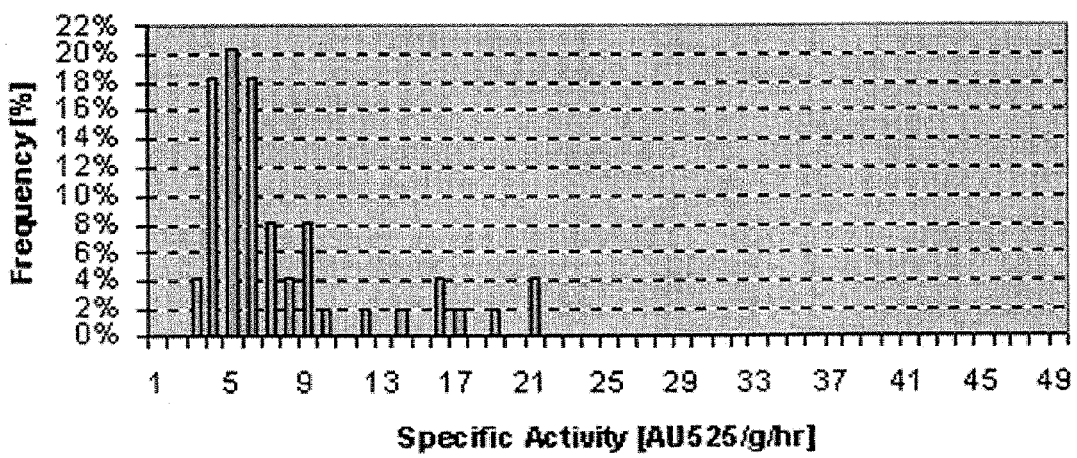
FIG. 7 shows the differences in dispersion of the genetic variability in the dehalogenase activity on the halogenated xenobiotic, 2,4,6-trichlorophenol (TCP).
Figure 7:
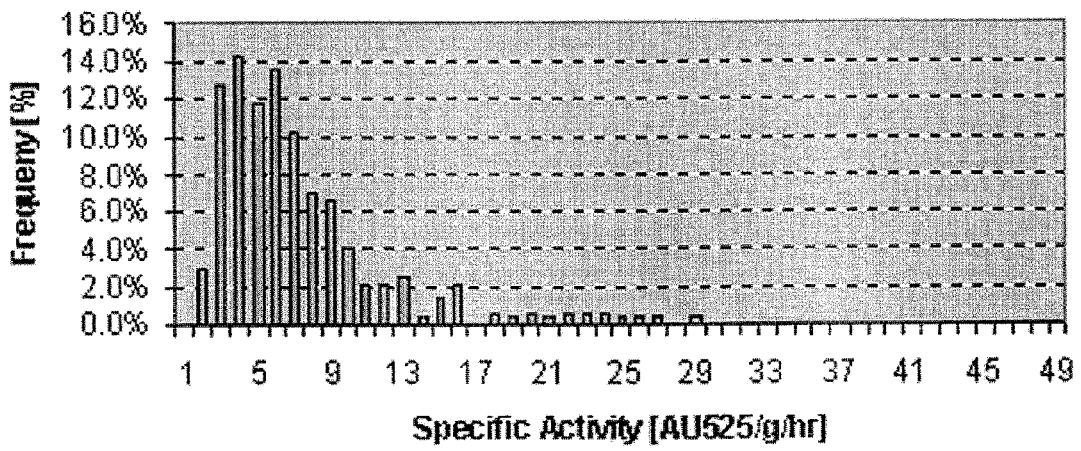
Figure 7:
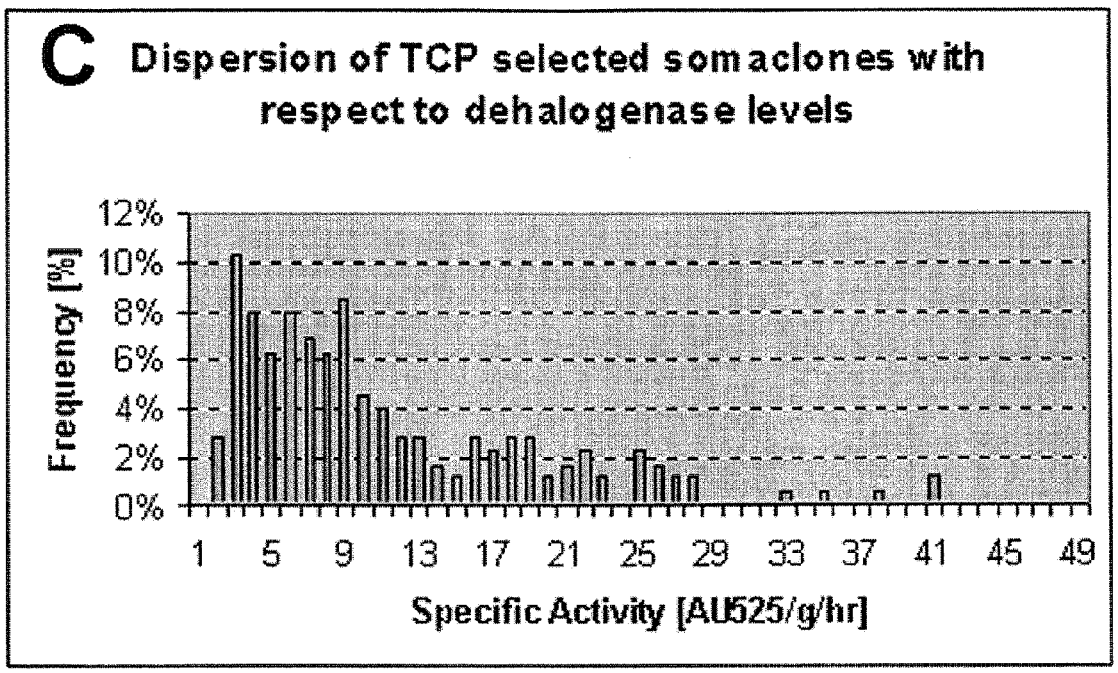
Figure 7:
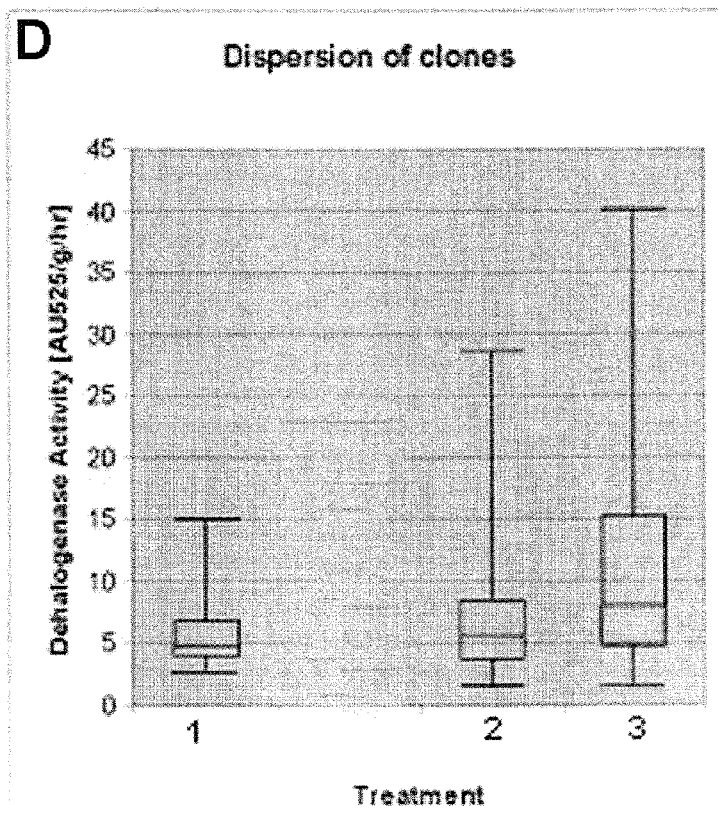

The application of a selection pressure alters the frequency of somaclonal variants. Exposure to near lethal levels of TCP results in greater genetic variability as assayed by dehalogenation activity. FIG. 7 demonstrates the dispersion of the genetic variability resulting from these experiments. The activity, standardized to fresh weight, is subdivided into arbitrary 1-unit ranges and the relative number (% of total tested) of individuals falling into the range is indicated on the Y axis of FIGS. 7A, 7B and 7C. Compared to nursery propagation by cuttings as shown in FIG. 7A, the embryogenic cell culture based propagation shown in FIG. 7B resulted in a 14% increase in the mean dehalogenation activity of the population above the $95^{th}$ percentile (top 5%). For the top 1%, the increase was 31%.

Additionally, exposure of the embryogenic cultures to near lethal levels of TCP resulted in greater genetic variation in the final plant population as assayed by dehalogenation activity and shown in FIG. 7C. FIG. 7C shows the increase of mean activity of the population above the $95^{th}$ percentile (top 5%) was 64% as compared to vegetative propagation. For the top 1%, the increase was 93%. FIG. 7D also presents the data charted as quartiles.

Example 5

Prescreen for Compatible Versus Incompatible Plant-microbe Associations

In order to determine which plant-microbe associations are compatible and which are not, prescreening of the various associations can be undertaken.

For this prescreening assay, excised sterile *Arundo donax* roots are dipped into liquid cultures of individual strains of bacteria and the roots are placed in quaternary plant culture medium, liquid or solidified with a gelling agent. Non-compatible bacteria cause discoloration, infiltration, hypersensitive reactions and finally necrosis of the roots. Compatible strains in which the roots remain normal are re-tested with intact plants.

Example 6

Figure 8:
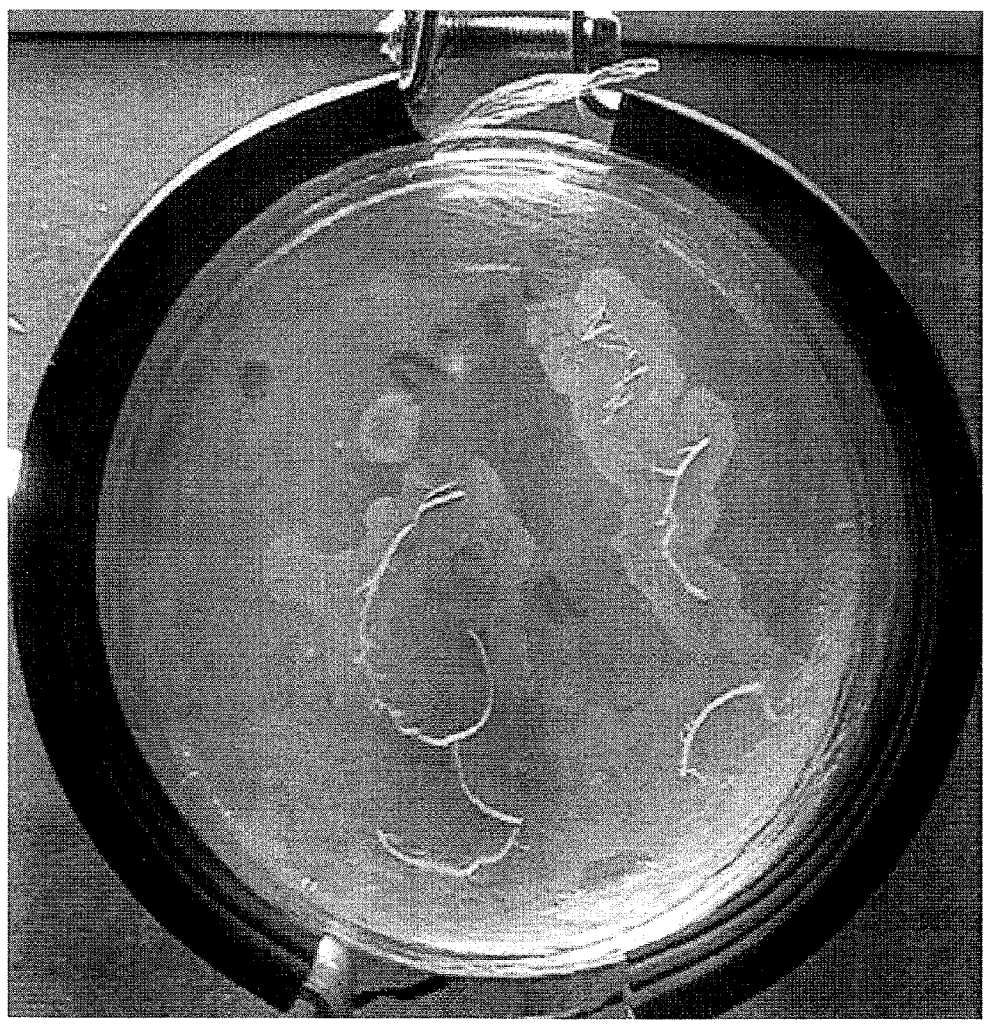
FIG. 8 shows an example of a microfilm degradation assay. *Arundo donax* roots colonized by bacteria (*Pseudomonas cepaica*) show clearing around the roots where the oil film is digested.

Oil Degradation in Plant-microbe Associations as Detected by a Microfilm Degradation Assay Disappearance of crude oil residue and select polyaromatic hydrocarbons in contact with bacteria-colonized roots can be visualized by a microfilm degradation assay. A thin film of crude oil is dried on the surface of minimal nutrient medium without carbon source by evaporation from a nonpolar solvent (for example, hexane) solution. The contrast between the oil film and the region cleared up by the bacteria (showing up as opaque) colonizing the roots is visualized by the photographic technique, which produces an opaque (whitish) appearance due to an opaque paper showing through the clear window created by the digestion of the oil film. FIG. 8 shows an example of a microfilm degradation assay in which *Arundo donax* roots are colonized by *Pseudomonas cepaica*.

The foregoing is illustrative of the present invention, and is not to be construed as limiting thereof. The invention is defined by the following claims, with equivalents of the claims to be included therein.

That which is claimed is:

1. A method of producing and maintaining a sustained totipotent embryogenic cell culture of a monocotyledonous plant comprising:

(a) cultivating an explant of tissue from a monocotyledonous plant shoot tip to produce a sustained totipotent embryogenic cell culture, wherein the monocotyledonous plant is selected from the group consisting of *Arundo* spp. and *Miscanthus* spp.;

(b) treating the sustained totipotent embryonic cell culture produced in step (a) with a cold temperature, wherein the cold temperature treatment is for a duration from about 60 days to about 360 days and comprises a temperature in a range from about 4 ° C. to about 10 ° C.;

(c) removing the sustained totipotent embryogenic cell culture from the cold temperature treatment; and (d) cultivating the sustained totipotent embryogenic cell culture, whereby the sustained totipotent embryogenic cell culture of the monocotyledonous plant has an increased growth rate of the embryogenic cell mass as compared to a control.

2. The method of claim 1, wherein the shoot tip is an inflorescence.

3. The method of claim 1, wherein the shoot tip is an immature inflorescence.

4. The method of claim 1, wherein steps (b) and (c) are carried out in the dark.

5. The method of claim 1, further comprising micropropagating a monocotyledonous plant, the method comprising transferring the sustained totipotent embryogenic cell culture of step (c) to a tertiary medium to continue multiplication and to produce a plantlet with roots and shoots.

6. The method of claim 5, comprising transferring the plantlet directly to soil for acclimatization to non-sterile and photosynthetic conditions and production of an acclimatized plantlet or plant.

7. The method of claim 1, wherein the treating of the sustained totipotent embryogenic cell culture with a cold temperature comprises exposing the sustained totipotent embryogenic cell culture of step (a) to at least one cold treatment.

8. The method of claim 7, wherein the treating with a cold temperature occurs in the dark.

9. The method of claim 7, wherein the treating with a cold temperature is for a duration from about 60 days to about 90 days.

10. The method of claim 7, wherein the treating with a cold temperature is for a duration of up to 360 days without subculture or with at least one subculture.

11. The method of claim 1, wherein the sustained totipotent embryogenic cell culture is stored long-term at a cold temperature.

12. The method of claim 11, wherein the long-term storage at a cold temperature is without subculturing of the sustained totipotent embryogenic cell culture.

13. The method of claim 1, wherein the explant of step (a) and/or the cell culture of step (c) is cultivated on a primary medium comprising auxin and cytokinin, further wherein the auxin is selected from the group consisting of 2,4-dichlorophenoxyacetic acid, picloram, and indolebutyric acid, and any combination thereof, and the cytokinin is selected from the group consisting of thidiazuron, zeatin, benzyladenine, kinetin, adenine hemisulfate and dimethylallyladenine, and any combination thereof.

14. The method of claim 1, wherein the explant of step (a) and/or the cell culture of step (c) is cultivated on a primary medium comprising auxin and cytokinin, further wherein the auxin is selected from the group consisting of 2,4-dichorophenoxyacetic acid, indolebutyric acid, and picloram, and any combination thereof, and the cytokinin is selected from the group consisting of adenine hemisulfate, dimethylallyladenine, zeatin, and thidiazuron, and any combination thereof.

15. The method of claim 14, wherein the auxin and cytokinin in the primary medium are present in the following concentrations: 2,4-dichlorophenoxyacetic acid, about 0.5 mg/l; indolebutyric acid, about 1.0 mg/l; picloram, about 0.12 mg/l; adenine hemisulfate, about 80 mg/l; dimethylallyladenine, about 0.5 mg/l; zeatin, about 0.5 mg/l; and thidiazuron, about 3 mg/l.

16. The method of claim 1, wherein the sustained totipotent embryogenic cell culture of step (d) is further cultivated on a secondary medium comprising auxin and cytokinin.

17. The method of claim 16, wherein the auxin is 2,4-dichlorophenoxyacetic acid which is present in a concentration of about 0.2 mg/l and the cytokinin is thidiazuron which is present in a concentration of about 0.02 mg/l.

18. The method of claim 1, wherein the explant is selected from a transgenic plant stably transformed with at least one heterologous nucleotide sequence.

19. The method of claim 1, further comprising introducing at least one heterologous nucleotide sequence into a cell of the sustained totipotent embryogenic cell culture to produce a transgenic sustained totipotent embryogenic cell culture.

20. The method of claim 19, wherein the heterologous nucleotide sequence is introduced into the cell of the sustained totipotent embryogenic cell culture by co-cultivation of the cell of the sustained totipotent embryogenic cell culture with *Agrobacterium tumefaciens* to produce a transgenic totipotent embryogenic cell culture.

21. The method of claim 19, further comprising producing a transgenic plantlet and/or plant from the transgenic sustained totipotent embryogenic cell culture.

22. A method of producing an elite plant line comprising: selecting for at least one trait of interest in the plantlet of claim 5, wherein the at least one trait of interest is a result of somaclonal variation or the introduction of at least one heterologous nucleotide sequence into the genome of a cell of the plantlet; and cultivating the plantlet comprising the at least one trait of interest to produce an elite plant line.

23. The method of claim 22, wherein the at least one trait of interest is chemical resistance and/or increased tolerance to an environmental condition.

24. A sustained totipotent tissue of a monocot plant that is produced by the method of claim 1.

25. A transgenic sustained totipotent tissue of a monocot plant that is produced by the method of claim 18.

26. The method of claim 1, wherein the explant is pretreated with a cold temperature prior to step (a).

27. The method of claim 1, wherein the sustained totipotent embryogenic cell culture produced in step (a) is transferred to a secondary medium prior to step (b).

* * * * *

UNITED STATES PATENT AND TRADEMARK OFFICE
CERTIFICATE OF CORRECTION

| | | |
|---|---|---|
| PATENT NO. | : 7,863,046 B2 | Page 1 of 1 |
| APPLICATION NO. | : 11/800719 | |
| DATED | : January 4, 2011 | |
| INVENTOR(S) | : Márton et al. | |

It is certified that error appears in the above-identified patent and that said Letters Patent is hereby corrected as shown below:

In the Specification:

Column 1, Lines 5-10: Please delete heading and paragraph:
"STATEMENT OF GOVERNMENT SUPPORT The present invention was funded in part by government support under grant number 10049180 from the National Institutes of Health. The United States Government has certain rights in this invention."

Column 12, Line 51: Please correct "2,4-dichiorophenoxyacetic"
to read -- 2,4-dichlorophenoxyacetic --

Column 17, Line 63: Please correct "KH2" to read -- $KH_2$ --

In the Claims:

Column 30, Claim 14, Lines 4-5: Please correct "2,4-dichorophenoxyacetic"
to read -- 2,4-dichlorophenoxyacetic --

Signed and Sealed this
Fifth Day of July, 2011

David J. Kappos
*Director of the United States Patent and Trademark Office*